US006911462B2

(12) United States Patent
Sircar et al.

(10) Patent No.: US 6,911,462 B2
(45) Date of Patent: Jun. 28, 2005

(54) BENZIMIDAZOLE COMPOUNDS FOR REGULATING IGE

(75) Inventors: Jagadish C. Sircar, San Diego, CA (US); Mark L. Richards, San Diego, CA (US); Michael G. Campbell, Durham, NC (US); Michael W. Major, Mequon, WI (US)

(73) Assignee: Avanir Pharmaceuticals, San Diego, CA (US)

( * ) Notice: Subject to any disclaimer, the term of this patent is extended or adjusted under 35 U.S.C. 154(b) by 11 days.

(21) Appl. No.: 10/103,258

(22) Filed: Mar. 20, 2002

(65) Prior Publication Data

US 2003/0100582 A1 May 29, 2003

Related U.S. Application Data

(63) Continuation-in-part of application No. 09/422,304, filed on Oct. 21, 1999, now Pat. No. 6,369,091, which is a continuation-in-part of application No. 09/316,870, filed on May 21, 1999, now Pat. No. 6,271,390.
(60) Provisional application No. 60/086,494, filed on May 21, 1998.

(51) Int. Cl.$^7$ ..................... A61K 31/415; A61K 31/44; C07D 401/12; C07D 403/12
(52) U.S. Cl. ...................... 514/393; 514/394; 514/336; 514/341; 514/338; 548/302.7; 548/309.7; 548/306.1; 548/268.1; 548/273.4
(58) Field of Search ................................ 514/394, 336, 514/341, 338; 548/302.7, 309.7, 306.1, 268.1, 273.4

(56) References Cited

U.S. PATENT DOCUMENTS

| | | | |
|---|---|---|---|
| 6,153,631 A | | 11/2000 | Petrie et al. |
| 6,271,390 B1 | * | 8/2001 | Sircar et al. ............. 548/309.7 |
| 6,303,645 B1 | * | 10/2001 | Sircar et al. ................. 514/394 |
| 6,369,091 B1 | * | 4/2002 | Sircar et al. ................. 514/394 |
| 6,387,938 B1 | | 5/2002 | Mizuguchi et al. |

FOREIGN PATENT DOCUMENTS

| | | |
|---|---|---|
| EP | 0 221 346 | 5/1987 |
| EP | 0 232 199 | 8/1987 |
| EP | 0 469 477 A1 | 2/1992 |
| EP | 0 497 564 A1 | 8/1992 |
| EP | 0 700 906 A1 | 3/1996 |
| EP | 719765 | 3/1996 |
| EP | 0 719 765 A2 | 7/1996 |
| WO | 98/17267 | 4/1987 |
| WO | 90/09989 | 9/1990 |
| WO | 93/25517 | 12/1993 |
| WO | WO 9961019 | 2/1999 |
| WO | WO 99 61020 | 2/1999 |
| WO | WO 8906975 | 8/1999 |
| WO | WO 0026192 | 5/2000 |
| WO | WO 0029384 | 5/2000 |

OTHER PUBLICATIONS

Ashton et al., New Low–Density Lipoprotein Receptor Upregulators Acting via a Novel Mechanism, Journal of Medicinal Chemistry, vol. 39, Jan. 1, 1996, pp. 3343–3356.
Synthesis of 32–(Subtitutephenyl) Benzimidazole Derivatives and their Sedative Activity: Structure–activity Relationships, Journal Fac. Pharm. Gazi University, vol. 7, No. 2, 1990, pp. 111–124.
S. Kanag'ozov, Synthesis of N–acyl derivatives of 6–amino–1–4–benzodioxane STN International, vol. 39, No. 1989, pp. 5–8, Abstract only.
B.V. Cheney et al., Structure–activity Correlations for a Series of Antiallergy Agents. 3. Development of a Quantitative Model, Journal Med. Chem., vol. 26, No. 5, 1983, pp. 726–737.
Japanese Application No. 10273013, entitled Antagonist for Gonadotrophic Hormone–Releasing Hormone, filed on Sep. 28, 1996, English abstract only.
Database Crossifre Beilstein 'Onlinel, Beilstein Institut zur Forderung der Chemisehen Wissenchaften, Frankfurt am Main, DE; Beilstein Registry No. 563073 & Khim. Farm. ZH., vol. 22, No. 6, 1988, pp. 697–699, (english translation).
Denny W A et al., "Potential antitumor agents. 59. Structure–activity relationships for 2–phenylbenzimidazole–4–carboxamides, a new class of "minimal" DNA–intercalating agents which may not act via topolsomerase II", Journal of Medicinal Chemistry, vol. 33, No. 2, Feb. 1990, pp. 814–819.
White A W et al., "Resistance–modifying agents. 9. Synthesis and biological properties of benzimidazole inhibitors of the DNA repair enzyme poly(ADP–ribose) polymerase", Journal of Medicinal Chemistry, vol. 43, No. 2, Nov. 2, 2000, pp. 4084–4097.
Database Caplus 'Onlinel Chemical Abstracts Service, Columbus, Ohio, US; Databse accession No. 2000:214835 & JP 2000 095767 (Takeda Chemical Industries, Ltd.), Apr. 4, 2000.
Kreimeyer A et al., "Suramin analogues with a 2–phenylbenzimidazole moiety as partyial structure; potential anti HIV– and anglostic drugs,2: Sulfanitic acid, benzendisulfonic, and naphthalanetrisulfonic acid analogues" Archi Der Pharmazie, vol. 331, No. 3, Mar. 1998, pp. 97–103.
Pozdnyakov et al. "Mass Spectrometric study of dissociative ionization of low–molecular models of aromatic polyamides" Khim. Vys. Energ. (1987), 21(1), 38–44 Coden: Khvkao; ISSN: 0023–1193, 1987.

* cited by examiner

Primary Examiner—Sreeni Padmanabhan
Assistant Examiner—Jennifer Kim
(74) Attorney, Agent, or Firm—Knobbe, Martens Olson & Bear LLP

(57) ABSTRACT

This invention relates to a family of phenylbenzimidazole analogs, which are inhibitors of the IgE response to allergens. These compounds are useful in the treatment of allergy and/or asthma or any diseases where IgE is pathogenic.

18 Claims, No Drawings

BENZIMIDAZOLE COMPOUNDS FOR REGULATING IGE

CROSS-REFERENCE TO RELATED APPLICATIONS

This application is a continuation-in-part application of U.S. application Ser. No. 09/422,304, filed on Oct. 21, 1999, now U.S. Pat. No. 6,369,091, which is a continuation-in-part of U.S. application Ser. No. 09/316,870, filed on May 21, 1999, now U.S. Pat. No. 6,271,390, which claims priority under 35 U.S.C. § 119(e) to U.S. Provisional Application No. 60/086,494, filed May 21, 1998, all herein incorporated by reference.

BACKGROUND OF THE INVENTION

1. Field of Invention

This invention relates to small molecule inhibitors of the IgE response to allergens that are useful in the treatment of allergy and/or asthma or any diseases where IgE is pathogenic.

2. Description of the Related Art

An estimated 10 million persons in the United States have asthma, about 5% of the population. The estimated cost of asthma in the United States exceeds $6 billion. About 25% of patients with asthma who seek emergency care require hospitalization, and the largest single direct medical expenditure for asthma has been inpatient hospital services (emergency care), at a cost of greater than $1.6 billion. The cost for prescription medications, which increased 54% between 1985 and 1990, was close behind at $ 1.1 billion (Kelly, *Pharmacotherapy* 12:13 S-2 IS (1997)).

According to the National Ambulatory Medical Care Survey, asthma accounts for 1% of all ambulatory care visits, and the disease continues to be a significant cause of missed school days in children. Despite improved understanding of the disease process and better drugs, asthma morbidity and mortality continue to rise in this country and worldwide (U.S. Department of Health and Human Services; 1991, publication no. 91-3042). Thus, asthma constitutes a significant public health problem.

The pathophysiologic processes that attend the onset of an asthmatic episode can be broken down into essentially two phases, both marked by bronchoconstriction, that causes wheezing, chest tightness, and dyspnea. The first early phase asthmatic response is triggered by allergens, irritants, or exercise. Allergens cross-link immunoglobulin E (IgE) molecules bound to receptors on mast cells, causing them to release a number of preformed inflammatory mediators, including histamine. Additional triggers include the osmotic changes in airway tissues following exercise or the inhalation of cold, dry air. The second, late phase response that follows is characterized by infiltration of activated eosinophils and other inflammatory cells into airway tissues, epithelial desquamonon, and by the presence of highly viscous mucus within the airways. The damage caused by this inflammatory response leaves the airways "primed" or sensitized, such that smaller triggers are required to elicit subsequent asthma symptoms.

A number of drugs are available for the palliative treatment for the palliative treatment of asthma; however, their efficacies vary markedly. Short-acting $\beta_2$-adrenergic agonists, terbutaline and albuterol, long the mainstay of asthma treatment act primarily during the early phase as bronchodilators. The newer long-acting $\beta_2$-agonists, salmeterol and formoterol, may reduce the bronchoconstrictive component of the late response. However, because the $\beta_2$-agonists do not possess significant antiinflammatory activity, they have no effect on bronchial hyperreactivity.

Numerous other drugs target specific aspects of the early or late asthmatic responses. For example, antihistamines, like loratadine, inhibit early histamine-mediated inflammatory responses. Some of the newer antihistamines, such as azelastine and ketotifen, may have both antiinflammatory and weak bronchodilatory effects, but they currently do not have any established efficacy in asthma treatment. Phosphodiesterase inhibitors, like theophylline/xanthines, may attenuate late inflammatory responses, but there is no evidence that these compounds decrease bronchial hyperreactivity. Anticholinergics, like ipratopium bromide, which are used in cases of acute asthma to inhibit severe bronchoconstriction have no effect on early or late phase inflammation, no effect on bronchial hyperreactivity, and therefore, essentially no role in chronic therapy.

The corticosteroid drugs, like budesonide, are the most potent antiinflammatory agents. Inflammatory mediator release inhibitors, like cromolyn and nedocromil, act by stabilizing mast cells and thereby inhibiting the late phase inflammatory response to allergen. Thus, cromolyn and nedocromil, as well as the corticosteroids, all reduce bronchial hyperreactivity by minimizing the sensitizing effect of inflammatory damage to the airways. Unfortunately, these antiinflammatory agents do not produce bronchodilation.

Several new agents are currently being developed that inhibit specific aspects of asthmatic inflammation. For instance, leukotriene receptor antagonists (ICI-204, 219, accolate), specifically inhibit leukotriene-mediated actions. The leukotrienes have been implicated in the production of both airway inflammation and bronchoconstriction.

Thus, while numerous drugs are currently available for the treatment of asthma, these compounds are primarily palliative and/or have significant side effects. Consequently, new therapeutic approaches which target the underlying cause rather than the cascade of symptoms would be highly desirable. Asthma and allergy share a common dependence on IgE-mediated events. Indeed, it is known that excess IgE production is the underlying cause of allergies in general and allergic asthma in particular (Duplantier and Cheng, *Ann. Rep. Med. Chem.* 29:73–81 (1994)). Thus, compounds that lower IgE levels may be effective in treating the underlying cause of asthma and allergy.

None of the current therapies eliminate the excess circulating IgE. The hypothesis that lowering plasma IgE may reduce the allergic response, was confirmed by recent clinical results with chimeric anti-IgE antibody, CGP-51901, and recombinant humanized monoclonal antibody, rhuMAB-E25. Indeed, three companies, Tanox Biosystems, Inc., Genentech Inc., and Novartis AG are collaborating in the development of a humanized anti-IgE antibody (BioWorld® Today, Feb. 26, 1997, p. 2) which will treat allergy and asthma by neutralizing excess IgE. Tanox has already successfully tested the anti-IgE antibody, CGP-51901, which reduced the severity and duration of nasal symptoms of allergic rhinitis in a 155-patient Phase II trial (Scrip #2080, Nov. 24, 1995, p. 26). Genentech recently disclosed positive results from a 536 patient phase II/III trials of its recombinant humanized monoclonal antibody, rhuMAB-E25 (BioWorld® Today, Nov. 10, 1998, p. 1). The antibody, rhuMAB-E25, administered by injection (highest dose 300 mg every 2 to 4 weeks as needed) provided a 50% reduction in the number of days a patient required additional "rescue" medicines (antihistamines and decongestants), compared to placebo. An NDA filing for this product is projected to be in the year 2000. The positive results from anti-IgE antibody trials suggest that therapeutic strategies aimed at IgE down-regulation may be effective.

SUMMARY OF THE INVENTION

Various preferred embodiments disclose a family of related compounds for use in the treatment of a condition associated with an excess IgE level. The phenylbenzimidazole inhibitors of IgE in accordance with various embodiments are represented by the generic formula:

Genus (A)

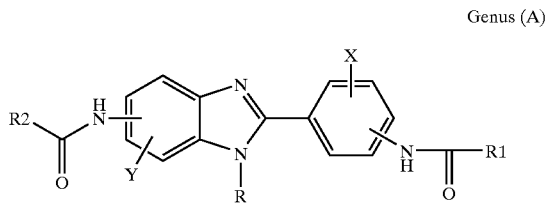

wherein X and Y are independently selected from the group consisting of mono, di, tri, and tetra substituted H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2C_6H_4$—F(p-);

wherein R1 and R2 are independently selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings, and substituted heterocyclic rings;

wherein R1 and R2 cannot both be methyl groups:

wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl and substituted heterocyclic rings are selected from the group consisting of alkyl, acyl, aryl, $CF_3$, $CH_3$, $OCH_3$, OH, CN, $COOR_5$, COOH, $COCF_3$, and heterocyclic rings; and wherein at least one of R1, R2 or said substituents is a heterocyclic ring; and Genus (B)

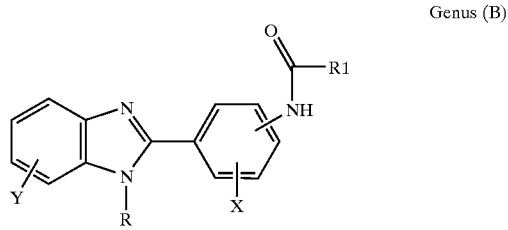

wherein X is selected from the group consisting of mono, di, tri, and tetra substituted H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2CH_4$—F(p-);

wherein Y is selected from the group consisting of mono, di, tri, and tetra substituted H, alkyl, alkoxy, aryl, benzo, substituted aryl, hydroxy, halogen, amino, alkylamino, nitro, cyano, $CF_3$, $OCF_3$, COPh, $COOCH_3$, $CONH_2$, CONHR, NHCONHR1, and NHCOR1; and wherein R1 is selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings containing one or more heteroatoms, and substituted heterocyclic rings; and wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl, and substituted heterocyclic rings are selected from the group consisting of alkyl, aryl, $CF_3$, $CH_3$, $OCH_3$, OH, CN, $COOR_5$, COOH, and heterocyclic rings.

In accordance with another aspect of the preferred embodiments, there is disclosed a composition for use in the treatment of an allergic condition comprising the diamidophenylbenzimidazole inhibitor of IgE disclosed above and at least one additional active ingredient, combined in a pharmaceutically acceptable diluent. The additional active ingredients may be selected from the group consisting of short-acting $\beta_2$-adrenergic agonists, like terbutaline and albuterol, long-acting $\beta_2$-adrenergic agonists, like salmeterol and formoterol, antihistamines, like loratadine, azelastine and ketotifen, phosphodiesterase inhibitors, anticholinergic agents, corticosteroids, inflammatory mediator release inhibitors and leukotriene receptor antagonists. Allergic reactions, as used herein, are any conditions in which IgE is pathogenic, including asthma.

In accordance with another aspect of the preferred embodiments, there is disclosed a family of diamidophenylbenzimidazole compounds for use in the treatment of an allergic condition. These compounds, comprising structures S1–SX 110, are illustrated in the Detailed Description of the Preferred Embodiment section below.

In accordance with another aspect of the preferred embodiments, there is disclosed a family of monoamidobenzimidazole compounds for use in the treatment of an allergic condition. These compounds, comprising structures SX-SX 5111–5123, are illustrated in the Detailed Description of the Preferred Embodiment section below.

In accordance with another aspect of the preferred embodiments, there is disclosed a method for the preparation of a medicament for treatment of a condition associated with an excess IgE level. The medicament comprises one or more compounds having the general formula described above for Genus A and Genus B.

In accordance with another aspect of the preferred embodiments, there is disclosed a method of treating a mammal having a condition associated with an excess IgE level. The method comprises administering to the mammal an amount of one or more compounds sufficient to reduce IgE levels in the mammal. The compounds have the general formula described above for Genus A and Genus B.

In a variation of the above disclosed methods, at least one additional active ingredient may be administered in conjunction with the administration of the compound. The additional active ingredient may be combined with said compound in a pharmaceutically acceptable diluent and co-administered to the mammal. The additional active ingredient may be a short-acting β2-adrenergic agonist selected from the group consisting of terbutaline and albuterol. In a variation, the additional active ingredient may be a long-acting β2-adrenergic agonist selected from the group consisting of salmeterol and formoterol or an antihistamine selected from the group consisting of loratadine, azelastine and ketotifen. In another variation, the additional active ingredient may be a phosphodiesterase inhibitor, an anticholinergic agent, a corticosteroid, an inflammatory mediator release inhibitor or a leukotriene receptor antagonist.

The compound is preferably administered at a dose of about 0.001 mg to about 300 mg per kg body weight per day in divided doses for at least two consecutive days, more preferably, between about 0.01 mg and 100 mg per kg body weight per day in divided doses.

Other variations within the scope of the preferred embodiments may be more fully understood with reference to the following detailed description.

DETAILED DESCRIPTION OF THE PREFERRED EMBODIMENT

Various embodiments are directed to small molecule inhibitors of IgE which are useful in the treatment of allergy and/or asthma or in any diseases where IgE is pathogenic. The inhibitors may affect the synthesis, activity, release, metabolism, degradation, clearance and/or any other pharmacokinetic parameter of IgE. The particular compounds disclosed herein were identified by their ability to suppress IgE levels in both ex vivo and in vivo assays. Development and optimization of clinical treatment regimens can be monitored by those of skill in the art by reference to the ex vivo and in vivo assays described below.

Ex-vivo Assay

This assay begins with in vivo antigen priming and measures secondary antibody responses in vitro. The basic protocol was documented and optimized for a range of parameters including: antigen dose for priming and time span following priming, number of cells cultured in vitro, antigen concentrations for eliciting secondary IgE (and other Ig's) response in vitro, fetal bovine serum (FBS) batch that will permit optimal IgE response in vitro, the importance of primed CD4+ T cells and hapten-specific B cells, and specificity of the ELISA assay for IgE (Marcelletti and Katz, *Cellular Immunology* 13 5:471–489 (1991); incorporated herein by reference).

The actual protocol utilized for this project was adapted for a more high throughput analyses. BALB/cByj mice were immunized i.p. with 10 μg DNP-KLH adsorbed onto 4 mg alum and sacrificed after 15 days. Spleens were excised and homogenized in a tissue grinder, washed twice, and maintained in DMEM supplemented with 10% FBS, 100 U/ml penicillin, 100 μg/ml streptomycin and 0.0005% 2-mercaptoethanol. Spleen cell cultures were established (2–3 million cells/ml, 0.2 ml/well in quadruplicate, 96-well plates) in the presence or absence of DNP-KLH (10 ng/ml). Test compounds (2 μg/ml and 50 ng/ml) were added to the spleen cell cultures containing antigen and incubated at 37° C. for 8 days in an atmosphere of 10% $CO_2$.

Culture supernatants were collected after 8 days and Ig's were measured by a modification of the specific isotype selective ELISA assay described by Marcelletti and Katz (Supra). The assay was modified to facilitate high throughput. ELISA plates were prepared by coating with DNP-KLH overnight. After blocking with bovine serum albumin (BSA), an aliquot of each culture supernatant was diluted (1:4 in phosphate buffered saline (PBS) with BSA, sodium azide and Tween 20), added to the ELISA plates, and incubated overnight in a humidified box at 4° C. IgE levels were quantitated following successive incubations with biotinylated-goat antimouse IgE (b-GAME), AP-streptavidin and substrate.

Antigen-specific IgG1 was measured similarly, except that culture supernatants were diluted 200-fold and biotinylated-goat antimouse IGGI (b-GAMG1) was substituted for b-GAME. IgG2a was measured in ELISA plates that were coated with DNP-KLH following a 1:20 dilution of culture supernatants and incubation with biotinylated-goat antimouse IgG2a (b-GAMG2a). Quantitation of each isotype was determined by comparison to a standard curve. The level of detectability of all antibody was about 200–400 pg/ml and there was less than 0.001% cross-reactivity with any other Ig isotype in the ELISA for IgE.

In Vivo Assay

Compounds found to be active in the ex vivo assay (above) were further tested for their activity in suppressing IgE responses in vivo. Mice receiving low-dose radiation prior to immunization with a carrier exhibited an enhanced IgE response to sensitization with antigen 7 days later. Administration of the test compounds immediately prior to and after antigen sensitization, measured the ability of that drug to suppress the IgE response. The levels of IgE, IgG1 and IgG2a in serum were compared.

Female BALB/cByj mice were irradiated with 250 rads 7 hours after initiation of the daily light cycle. Two hours later, the mice were immunized i.p. with 2 μg of K.LH in 4 mg alum. Two to seven consecutive days of drug injections were initiated 6 days later on either a once or twice daily basis. Typically, i.p. injections and oral gavages were administered as suspensions (150 μl/injection) in saline with 10% ethanol and 0.25% methylcellulose. Each treatment group was composed of 5–6 mice. On the second day of drug administration, 2 μg of DNP-KLH was administered i.p. in 4 mg alum, immediately following the morning injection of drug. Mice were bled 7–21 days following DNP-KLH challenge.

Antigen-specific IgE, IgG1 and IgG2a antibodies were measured by ELISA. Periorbital bleeds were centrifuged at 14,000 rpm for 10 min, the supernatants were diluted 5-fold in saline, and centrifuged again. Antibody concentrations of each bleed were determined by ELISA of four dilutions (in triplicate) and compared to a standard curve: anti-DNP IgE (1:100 to 1:800), anti-DNP IgG2a (1:100 to 1:800), and anti-DNP IgG1 (1:1600 to 1:12800).

Phenylbenzimidazole Inhibitors of IgE

Several species embraced by the following generic formula were synthesized and evaluated for their effectiveness in down-regulating IgE in the ex vivo and in vivo assays. Genus A is illustrated below:

Genus (A)

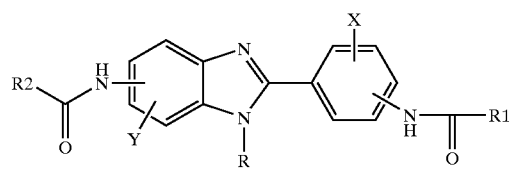

wherein X and Y are independently selected from the group consisting of mono, di, tri, and tetra substituted H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2C_6H_4$—F(p-);

wherein R1 and R2 are independently selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings, and substituted heterocyclic rings;

wherein R1 and R2 cannot both be methyl groups;

wherein the substituents on said substituted alkyl, substituted cycloalkyl, substituted cyclopropyl, substituted cyclobutyl, substituted.cyclopentyl, substituted cyclohexyl, substituted cycloheptyl, substituted bicycloalkenyl, substituted adamantyl and substituted heterocyclic rings are selected from the group consisting of alkyl, acyl, aryl, $CF_3$, $CH_3$, $OCH_3$, OH, CN, $COOR_5$, COOH, $COCF_3$, and heterocyclic rings; and wherein at least one of R1, R2 or said substituents is a heterocyclic ring.

Another related genus is the monoamido variation illustrated below:

Genus (B)

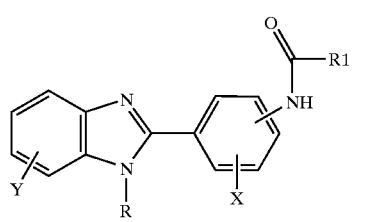

wherein X is selected from the group consisting of mono, di, tri, and tetra substituted H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2CH_4$—F(p-);

wherein Y is selected from the group consisting of mono, di, tri, and tetra substituted H, alkyl, alkoxy, aryl, benzo, substituted aryl, hydroxy, halogen, amino, alkylamino, nitro, cyano, $CF_3$, $OCF_3$, COPh, $COOCH_3$, $CONH_2$, CONHR, NHCONHR1, and NHCOR1; and wherein R1 is selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings containing one or more heteroatoms, and substituted heterocyclic rings; and wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl, and substituted heterocyclic rings are selected from the group consisting of alkyl, aryl, $CF_3$, $CH_3$, $OCH_3$, OH, CN, $COOR_5$, COOH, and heterocyclic rings.

Species embraced by Genus A and Genus B are provided later in this section.

General Organic Methods

HPLC/MS data was obtained using a Gilson semi-prep HPLC with a Gilson 170 Diode Array UV detector and PE Sciex API 100LC MS based detector. A Waters 600E with a Waters 490E UV detector was also used for recording HPLC data. The compounds were eluted with a gradient of $CH_3CN$ (with 0.0035% TFA) and H20 (with 0.01% TFA). Both HPLC instruments used Advantage C18 60A 5μ 50 mm×4.6 mm columns from Thomson Instrument Company. Mass spectra were obtained by direct injection and electrospray ionization on a PE Sciex API 100LC MS based detector. Thin layer chromatography was performed using Merck 60F-254 aluminum backed pre-coated plates. Flash chromatography was carried out on Merck silica gel 60 (230–400 mesh) purchased from EM Scientific.

Synthesis of the Combinatorial Library

The diamido-phenylbenzimidazole compounds of the preferred embodiments were prepared using the following synthetic reactions shown in Synthetic Scheme 1, wherein the desired acid chlorides are selected from the R1 and R2 groups provided in Table 1. The numbers that refer to the compounds in the text below correspond to those in the diagram. Compounds 1 and 2 can have the appropriate substituents to ultimately give a desired product 6 with the corresponding substituents. Table 1 discloses preferred acid chlorides and does not represent all the possible acid chlorides that can be used.

Synthetic Scheme 1

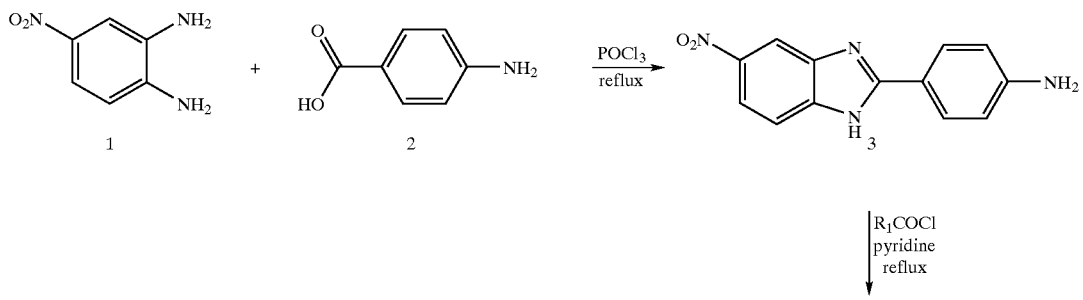

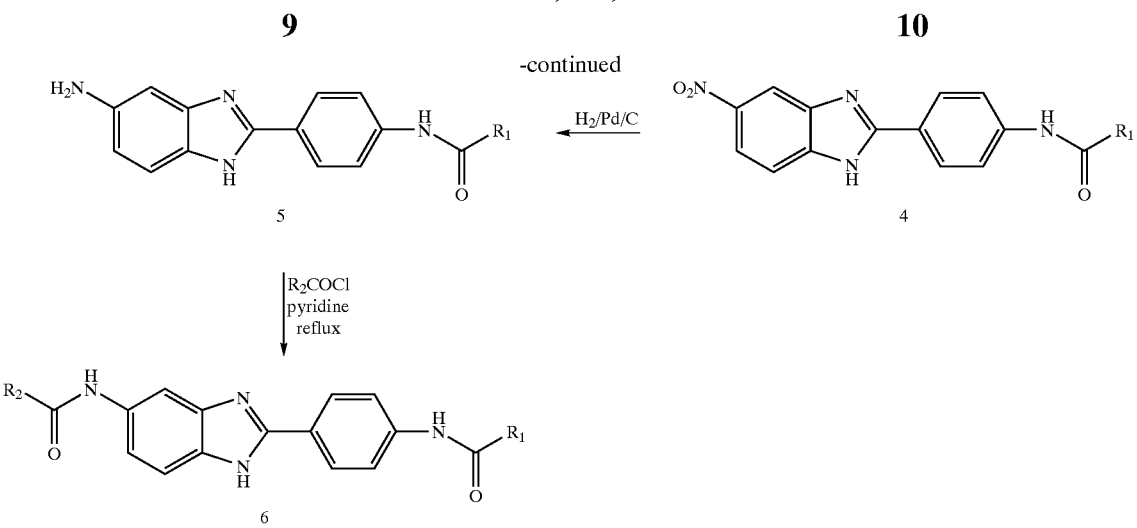

Synthesis of 3 4-Nitro-1,2-phenylenediamine (10 g, 65.3 mmol) and 4-aminobenzoic acid (8.95 g, 65.3 mmol) were taken in a round bottomed flask and phosphorus oxychloride (95 ml) was added slowly. The reaction mixture was allowed to stir under reflux conditions. After 18 h, the reaction was allowed to cool and then poured slowly into an ice water mixture in an Erlenmeyer flask with vigorous stirring. Greenish yellow precipitate fell out which was then filtered and washed with copious amounts of water. The residue was then dried to obtain 16.9 g of crude desired product. Mass spectrum analysis (positive ion) indicated presence of phenylbenzimidazole 3.

Synthesis of 4 Phenylbenzimidazole 3 (800 mg, 3.14 mmol) was dissolved in dry pyridine (5 ml) in a scintillation vial and a desired acid chloride (1.1 eq) was added slowly. The reactions were carried out in an oven at 60° C. After 16 h, the reaction was cooled to RT and DI water was added. Precipitation took place, which was filtered off, washed with water and air-dried. The aqueous layer was extracted with EtOAc (6×50 ml), dried over anhydrous $Na_2SO_4$ and the solvent was removed in vacuo to result in a colored solid. By positive ion MS the desired monoamido product was found to be present in the initial precipitate as well as in the organic layer. Hence the solid residues obtained were combined and used as such for the reduction step.

Synthesis of 5 Crude monoamido-nitrobenzimidazole 4 (1.22 g, 3.40 mmol) was dissolved in MeOH (20 ml) and minimum amount of THF was added for complete dissolution to occur. Catalytic amount of 10% Pd on C was added and the solution was degassed and allowed to stir at 3.4 atm pressure under $H_2$ atmosphere for 4 h. Upon completion of reaction as observed via TLC, the reaction mixture was filtered through celite and the solvent was removed under reduced pressure to afford 979 mg of crude residue.

Synthesis of 6 Phenylbenzimidazole 5 was dissolved in dry pyridine in a scintillation vial and a desired acid chloride (1.1 eq) was added slowly. The reactions were carried out in an oven at 60° C. After 16 h, the reaction was cooled to RT and DI water was added. Precipitation took place, which was filtered off, washed with water and air-dried. The aqueous layer was extracted with EtOAc, dried over anhydrous $Na_2SO_4$ and the solvent was removed in vacuo to result in diamido product 6.

TABLE 1

| | R1 | | R2 |
|---|---|---|---|
| A | cyclohexanecarbonyl chloride | A | cyclohexanecarbonyl chloride |
| B | cyclopentanecarbonyl chloride | B | cyclopentanecarbonyl chloride |
| C | cycloheptanecarbonyl chloride | C | cycloheptanecarbonyl chloride |
| D | norbornanecarbonyl chloride | D | norbornanecarbonyl chloride |
| E | norbornenecarbonyl chloride | E | norbornenecarbonyl chloride |
| F | adamantanecarbonyl chloride | F | adamantanecarbonyl chloride |

TABLE 1-continued

| R1 | R2 |
|---|---|

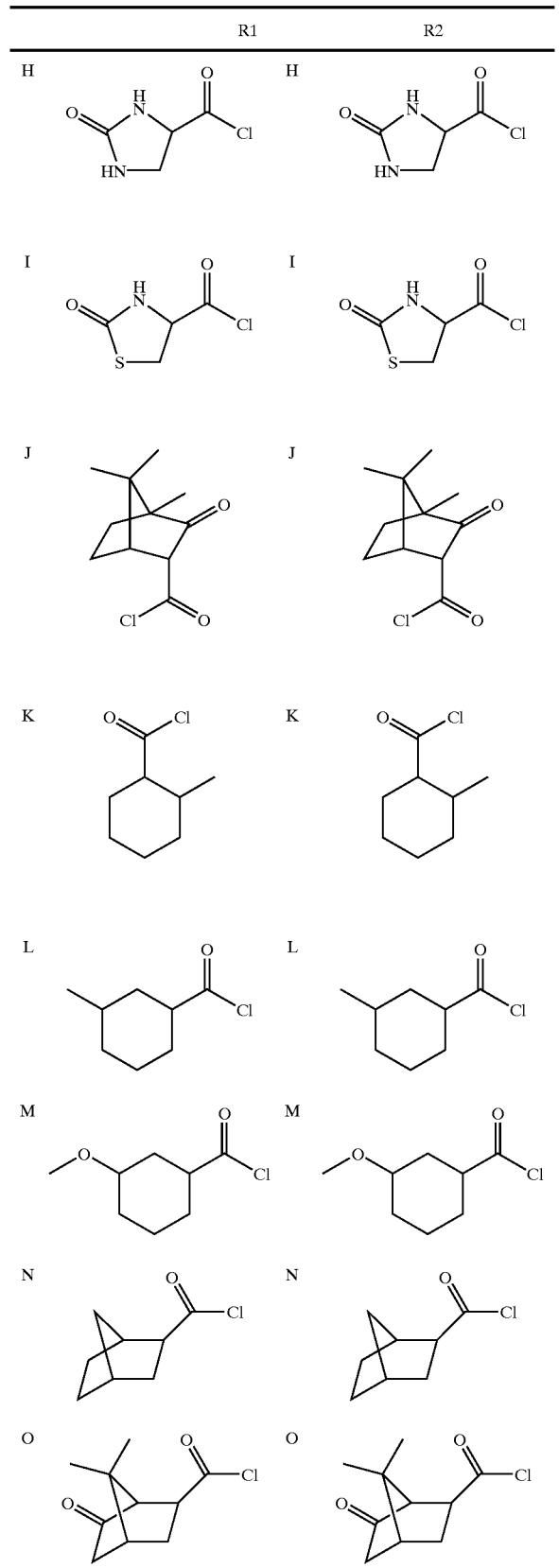
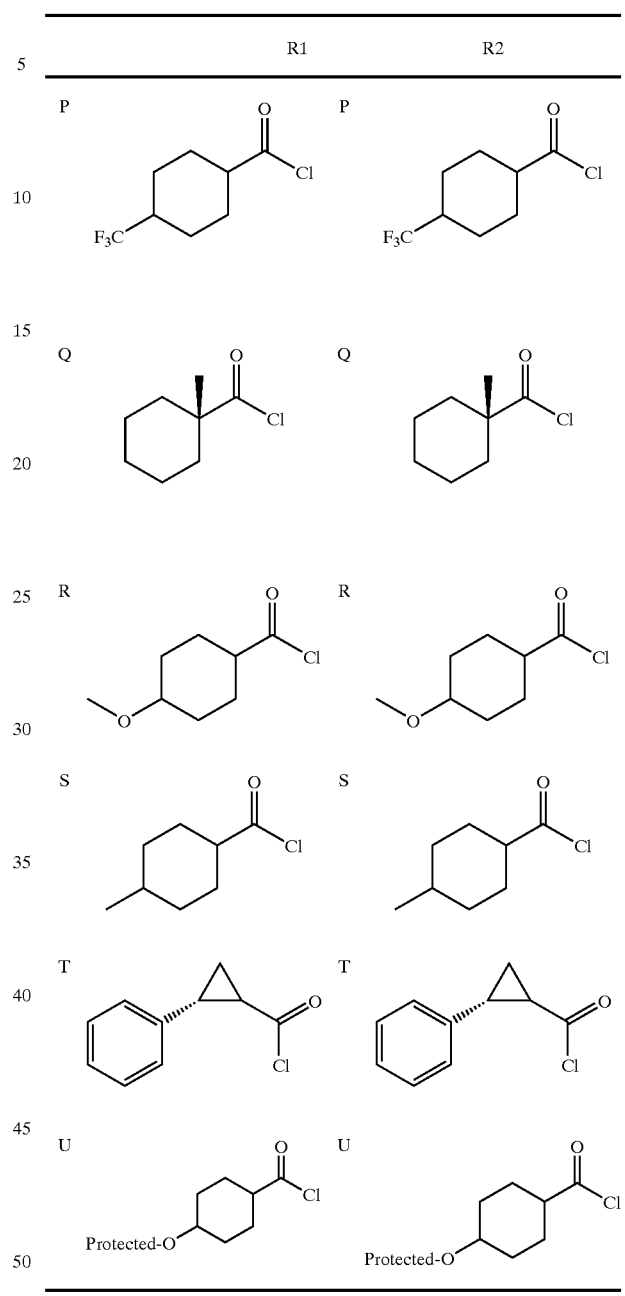

The monoamido-phenylbenzimidazole compounds of the preferred embodiments were prepared using the following synthetic reactions shown in Synthetic Scheme 2, wherein the desired acid chlorides are selected from the R1 and R2 groups provided in Table 1. Again, Table 1 discloses preferred acid chlorides and does not represent all the possible acid chlorides that can be used. The reactions of Synthetic Scheme 2 are similar to the reactions of Synthetic Scheme 1. Accordingly, the conditions and reagents described for the reactions of Synthetic Scheme 1 may also be used for the reactions of Synthetic Scheme 2.

Synthetic Scheme 2

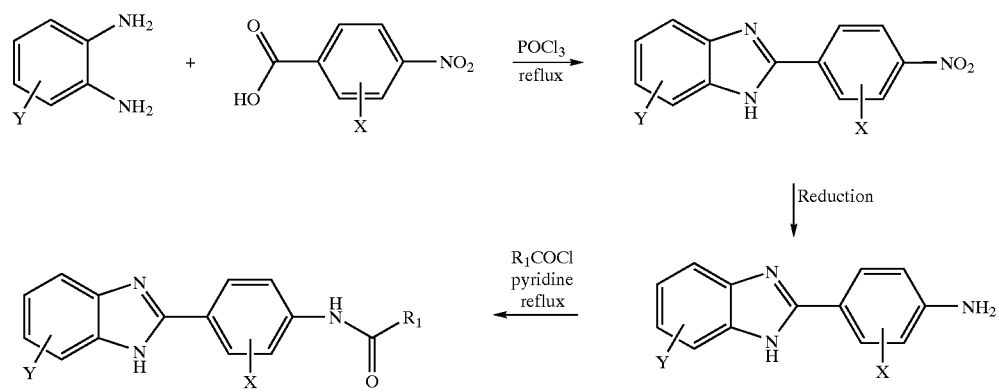

Intermediates to the Synthesis of Monoamido- and Diamido-phenylbenzimidazoles

The symmetrical diamido-phenylbenzimidazole compounds of the preferred embodiments were generally prepared from 2-(4-aminophenyl)-5-aminobenzimidazole, which was obtained by reduction of 2-(4-nitrophenyl)-5-nitrobenzimidazole.

S-125

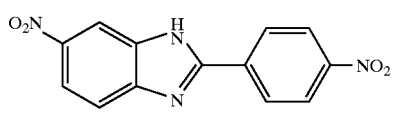

2-(4-nitrophenyl)-5-nitrobenzimidazole

The dinitro benzimidazole was prepared as follows: a mixture of 4-nitrophenylenediamine (6.4 g, 41.83 mmol) and 4-nitrobenzoic acid (7.86 g, 47 mmol) was dissolved in $POCl_3$ (250 ml) and heated to reflux for 2 h. The reaction mixture was cooled, poured on to ice, and stirred for 30 min. The resulting solid was filtered and washed with methanol and sodium bicarbonate to remove unreacted acid and allowed to dry overnight to give the desired product as a brown solid (5.8 g). The product was characterized by electrospray mass spectroscopy (mp>300° C.).

S-126

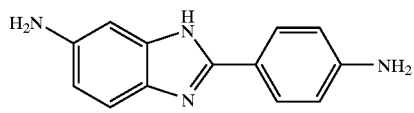

2-(4-aminophenyl)-5-aminobenzimidazole 2-(4-Aminophenyl)-5-aminobenzimidazole was prepared by suspending the above solid (75 g) in THF (75 ml), to which was added Pd—C (10% Pd by weight). The flask was purged with hydrogen and stirred under a balloon of hydrogen overnight. TLC and MS showed starting material was still present so the reaction was allowed to continue over the weekend. TLC indicated complete reaction, the reaction was filtered through celite and washed with methanol. The solvent was removed under reduced pressure to give a dark brown solid (0.37 g) that was used without further purification.

Alternatively, the 2-(4-aminophenyl)-5-aminobenzimidazole was prepared by the following reduction: 2-(4-nitrophenyl)-6-nitrobenzimidazole (8.9 g, 31 mmole) was suspended in concentrated HCl (100 ml) to which was added stannous chloride (42.3 g 180 mmole). The reaction mixture was heated to reflux for 5 hrs. The mixture was cooled to RT and the HCl salt of the desired product was precipitated by the addition of ethanol. The resulting solid was filtered, re-dissolved in water and the solution made basic by the addition of concentrated ammonium hydroxide. The resulting precipitate was filtered and dried overnight under vacuum to yield the desired product as a gray solid (6.023 g, 26.9 mmole, 87%). The product was characterized by electrospray mass spectroscopy and HPLC (mp. 222–227° C.).

S-127

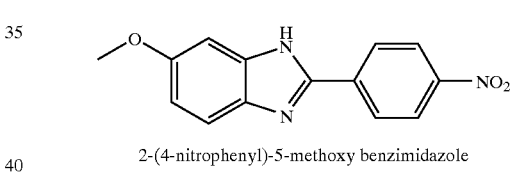

2-(4-nitrophenyl)-5-methoxy benzimidazole 2-(4-Aminophenyl)-5-methoxy benzimidazole was synthesized from 2-(4-nitrophenyl)-5-methoxy benzimidazole, which was prepared as follows: 1,2-diamino-4-methoxybenzene (1.26 g, 10.0 mmole) was mixed with 4-nitrobenzoic acid (1.67 g, 9.8 mmole) and dissolved in $POCl_3$ (10 ml) and heated to reflux for 2.5 hours. The reaction mixture was cooled and cautiously poured onto ice. The resulting solid was filtered, washed with $NaHCO_3$ and used with out further purification.

S-128

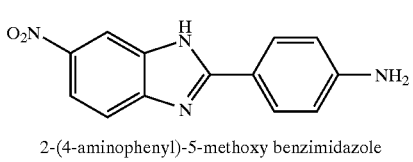

2-(4-aminophenyl)-5-methoxy benzimidazole 2-(4-Aminophenyl)-5-methoxy benzimidazole was prepared by dissolving 1.0 g of the above nitrobenzimidazole in 30% $Na_2S9H_2O$ (20 ml) with stirring at RT for 21 h. The reaction mixture was diluted with water and extracted with EtOAc. The combined organic extracts were dried over sodium sulfate and concentrated under vacuum. The product was characterized by mass spectroscopy.

S-129

2-(4-nitrophenyl)-5,6-dichloro benzimidazole 2-(4-Aminophenyl)-5,6-dichloro benzimidazole was synthesized from 2-(4-nitrophenyl)-5,6-dichloro benzimidazole, which was prepared as follows: 1,2-diamino-4,5-dichlorobenzene (1.68 g, 10.0 mmole) was mixed with 4-nitrobenzoic acid (1.58 g, 9.3 mmole), dissolved in POCl₃ (10 ml), and heated to reflux for 2.5 hours. The reaction mixture was cooled and cautiously poured onto ice. The resulting solid was filtered, washed with NaHCO₃ and used without further purification.

S-130

2-(4-Aminophenyl)-5,6-dichloro benzimidazole 2-(4-Aminophenyl)-5,6-dichloro benzimidazole was prepared by dissolving 1.0 g of the above nitrobenzimidazole in 30% Na₂S·9H₂O (20 ml) with stirring at RT for 21 h. The reaction mixture was diluted with water and extracted with EtOAc. The combined organic extracts were dried over sodium sulfate and concentrated under vacuum. The product was characterized by mass spectroscopy.

S-131

2-(4-nitrophenyl)-7-methyl benzimidazole 2-(4-aminophenyl)-7-methyl benzimidazole was synthesized from 2-(4-nitrophenyl)-7-methyl benzimidazole, which was prepared by mixing 1,2-diamino-3-methylbenzene (1.24 g, 10.0 mmole) with 4-nitrobenzoic acid (1.69 g, 9.8 mmole), dissolved in POCl₃ (10 ml), and heated to reflux for 2.5 hours. The reaction mixture was cooled and cautiously poured onto ice. The resulting solid was filtered, washed with NaHCO₃ and used without further purification.

S-132

2-(4-aminophenyl)-7-methylbenzimidazole 2-(4-Aminophenyl)-7-methyl benzimidazole was synthesized by dissolving 1.0 g of the above nitrobenzimidazole in 30% Na₂S·9H₂O (20 ml) with stirring at RT for 4.5 h. The reaction mixture was diluted with water and extracted with EtOAc. The combined organic extracts were dried over sodium sulfate and concentrated under vacuum. The product was characterized by mass spectroscopy.

S-133

2-(4-nitrophenyl)-6-methylbenzimidazole 2-(4-Aminophenyl)-6-methylbenzimidazole was synthesized from 2-(4-nitrophenyl)-6-methylbenzimidazole, which was prepared by mixing 1,2-diamino-4-methylbenzene (1.24 g, 9.80 mmole) with 4-nitrobenzoic acid (1.6 g, 9.9 mmole) and dissolved in POCl₃ (10 ml) and heated to reflux for 2.5 hours. The reaction mixture was cooled and cautiously poured onto ice. The resulting solid was filtered, washed with NaHCO₃ and used without further purification.

S-134

2-(4-aminophenyl)-6-methylbenzimidazole 2-(4-Aminophenyl)-6-methylbenzimidazole was synthesized by dissolving 1.0 g of the above nitrobenzimidazole in 30% Na₂S·9H₂O (20 ml) with stirring at RT for 4.5 h. The reaction mixture was diluted with water and extracted with EtOAc. The combined organic extracts were dried over sodium sulfate and concentrated under vacuum. The product was characterized by mass spectroscopy.

S-135

2-(4-nitrophenyl)-5,6-dimethylbenzimidazole 2-(4-Aminophenyl)-5,6-dimethylbenzimidazole was synthesized from 2-(4-nitrophenyl)-5,6-dimethylbenzimidazole, which was prepared by mixing 1,2-diamino-4,5-dimethylbenzene (1.38 g, 10.1 mmole) with 4-nitrobenzoic acid (1.69 g, 9.9 mmole) and dissolved in POCl₃ (10 ml) and heated to reflux for 2.5 hours. The reaction mixture was cooled and cautiously poured onto ice. The resulting solid was filtered, washed with NaHCO₃ and used without further purification.

S-136

2-(4-aminophenyl)-5,6-dimethylbenzimidazole 2-(4-Aminophenyl)-5,6-dimethylbenzimidazole was synthesized by dissolving 1.0 g of the above nitrobenzimidazole in 30% Na₂S·9H₂O (20 ml) with stirring at RT for 4.5 h. The reaction mixture was diluted with water and extracted with EtOAc. The combined organic extracts were dried over sodium sulfate and concentrated under vacuum. The product was characterized by mass spectroscopy.

The subsequent preparation of symmetrical diamides was accomplished by one of the following methods:

Method A: 2-(4-Aminophenyl)-6-aminobenzimidazole (1.0 mmole) was suspended in THF (5 ml) to which was added DIEA (2.5 mmole) and the mixture cooled to −78° C. To the above cooled mixture was added the acid chloride (2.5 mmole) and let warm to RT overnight. Water (2.0 ml) was added to the reaction and extracted with EtOAc. The combined organic extracts were combined washed with NaHCO$_3$ (aq.) and concentrated under reduced pressure. The resulting residue was purified on silica gel (hexanes/EtOAc or MeOH/CH$_2$Cl$_2$) or reverse phase HPLC (CH$_3$CN/H$_2$O).

Method B: 2-(4-Aminophenyl)-6-aminobenzimidazole (1.0 mmole) and DMAP (cat.) was dissolved in pyridine (5 ml). To the above solution was added the acid chloride (2.5 mmole) and the reaction stirred overnight at 60° C. The reaction was cooled to room temperature and water added to precipitate the product. The resulting solid was collected by filtration with the solid being washed with hexanes and water and NaHCO$_3$ (aq.). The resulting residue was purified on silica gel (hexanes/EtOAc or MeOH/CH$_2$Cl$_2$) or reverse phase HPLC (CH$_3$CN/H$_2$O).

Method C: 2-(4-Aminophenyl)-6-aminobenzimidazole (1.0 mmole) was suspended in THF (10 ml) to which was added K$_2$CO$_3$ (2.5 mmole) in water (0.5 ml). and the mixture cooled to −78° C. To the above cooled mixture was added the acid chloride (2.5 mmole) and let it warm to RT overnight. Water (10 ml) was added to the reaction and extracted with EtOAc. The combined organic extracts were combined, washed with NaHCO$_3$ (aq.) and concentrated under reduced pressure. The resulting residue was purified on silica gel (hexanes/EtOAc or MeOH/CH$_2$Cl$_2$) or reverse phase HPLC (CH$_3$CN/H$_2$O).

Method D: The carboxylic acid (2.2 mmole), EDC (2.2 mmole) and DMAP (cat.) was dissolved in hot pyridine. To the above solution was added 2-(4-aminophenyl)-6-aminobenzimidazole (1.0 mmole) and heated to 60° C. overnight. The cooled reaction mixture was partitioned between water and EtOAc. The organic layer was washed with NaHCO$_3$, dried over Na$_2$SO$_4$ and concentrated under vacuum. The resulting residue was purified on silica gel (hexanes/EtOAc or MeOH/CH$_2$Cl$_2$) or reverse phase HPLC (CH$_3$CN/H$_2$O).

Diamido-phenylbenzimidazole Species

The diamido-phenylbenzimidazole species encompassed within the disclosed generic formula were synthesized and tested for their ability to suppress IgE. The syntheses of several of these species are provided below.

(1)

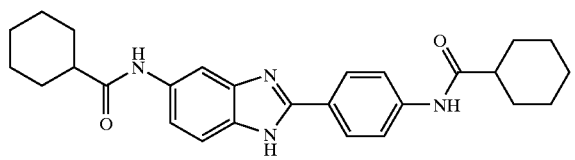

S-1

(1) 2-(N-Cyclohexylcarbonyl-4'-aminophenyl)-6-cyclohexylcarbonylamino)-benzimidazole was prepared by Method A from 2-(4-aminophenyl)-6-aminobenzimidazole (0.195 g, 0.87 mmole) and cyclohexylcarbonyl chloride (0.291 ml, 0.319 g, 2.175 mmole). The resulting solid (76.7 mg) was purified by preparative HPLC.

(2)

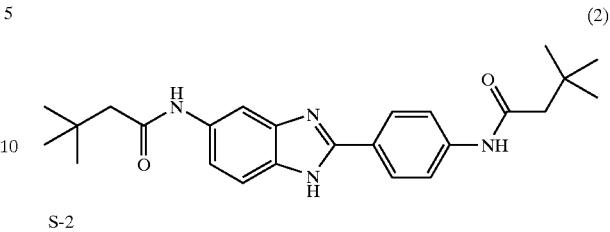

S-2

(2) Bis-t-butylacetyl benzimidazole was prepared by Method A from. 2-(4-aminophenyl)-6-amino-benzimidazole (0.195 g, 0.87 mmole) and t-butylacetyl chloride (0.302 ml, 0.292 g, 2.175 mmol). The resulting solid (42.3 mg) was purified by preparative HPLC.

(3)

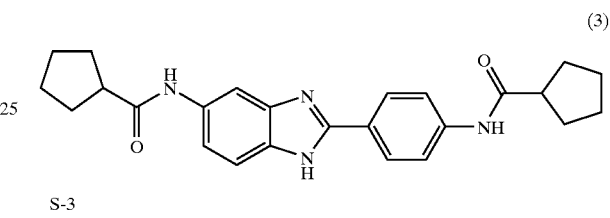

S-3

(3) Bis-cyclopentylcarbonyl benzimidazole was prepared by Method A from 2-(4-aminophenyl)-6-amino-benzimidazole (0.195 g, 0.87 mmole) and cyclopentylcarbonyl chloride (0.227 ml, 0.228 g, 2.175 mmol). The resulting solid (42.3 mg) was purified by preparative HPLC.

(4)

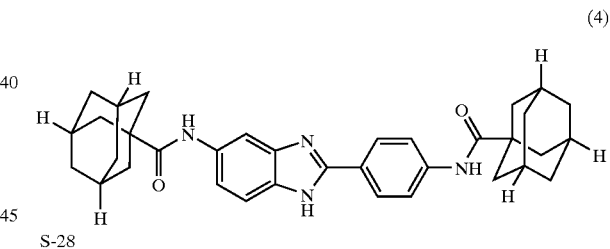

S-28

(4) Bis-adamantylcarbonyl benzimidazole was prepared by Method C from 2-(4-aminophenyl)-6-amino-benzimidazole (0.500 g, 2.23 mmole) and adamantylcarbonyl chloride (1.063 g, 5.35 mmol). The resulting solid was purified by preparative HPLC to give about 100 mg of 97% pure material.

(5)

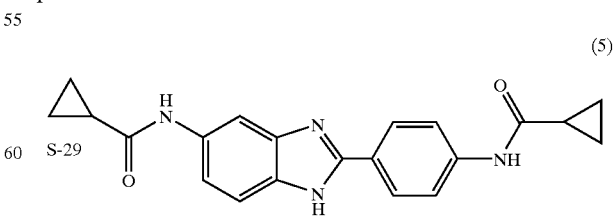

S-29

(5) Bis-cyclopropylcarbonyl benzimidazole was prepared by Method C from 2-(4-aminophenyl)-6-amino benzimidazole (0.500 g, 2.23 mmole) and cyclopropylcarbonyl chlo ride (0.485 ml, 0.559 g, 5.35 mmol). The resulting solid was purified on silica gel (5% MeOH in CH$_2$Cl$_2$). HPLC shows product is 94% pure.

(6)

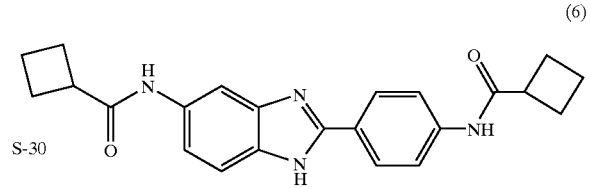

S-30

(6) Bis-cyclobutylcarbonyl benzimidazole was prepared by Method C from 2-(4-aminophenyl)-6-amino benzimidazole (0.500 g, 2.23 mmole) and cyclobutylcarbonyl chloride (0.610 ml, 0.634 g, 5.35 mmol). The resulting solid was purified on silica gel (5% MeOH in CH$_2$Cl$_2$). HPLC shows product is 97.4% pure.

(7)

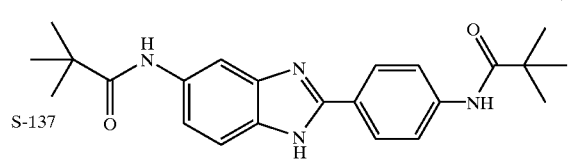

S-137

(7) Bis-trimethylacetyl benzimidazole was prepared by method C from 2-(4-aminophenyl)-6-amino benzimidazole (0.500 g, 2.23 mmole) and trimethylacetyl chloride (0.610 ml, 0.634 g, 5.35 mmol). The resulting solid was purified by re-crystallization (acetone/hexane) and shown to be 95% pure by HPLC.

(8)

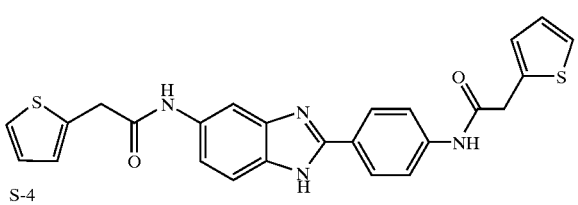

S-4

(8) Bis-2-thiopheneacetyl benzimidazole was prepared by method C from 2-(4-aminophenyl)-6-amino benzimidazole (0.500 g, 2.23 mmole) and thiopheneacetyl chloride (0.660 ml, 0.860 g, 5.35 mmol). The resulting solid was purified on silica gel (5% MeOH in CH$_2$Cl$_2$). HPLC shows the product is 92% pure.

(9)

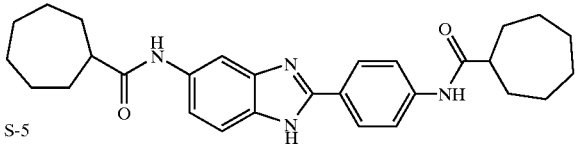

S-5

(9) Bis-cycloheptanecarbonyl benzimidazole was prepared by method C from 2-(4-aminophenyl)-6-amino benzimidazole (0.500 g, 2.23 mmole) and cycloheptanecarbonyl chloride (0.610 ml, 0.634 g, 5.35 mmol). The resulting solid was purified by preparative HPLC to give a solid that was 98.8% pure. The cycloheptanecarbonyl chloride was synthesized as follows: cycloheptane carboxylic acid (1.37 ml, 1.42 g, 10 mmole) was added to a dried 25 ml round bottom flask and purged with N$_2$. To the flask was added oxalyl chloride (7.5 ml, 2 M in CH$_2$Cl$_2$) via syringe followed by one drop DMF. The reaction was stirred at RT overnight and the reaction concentrated under vacuum. Methylene chloride (5 ml) was added and concentrated under vacuum to remove residual oxalyl chloride (repeated 5 times).

(10)

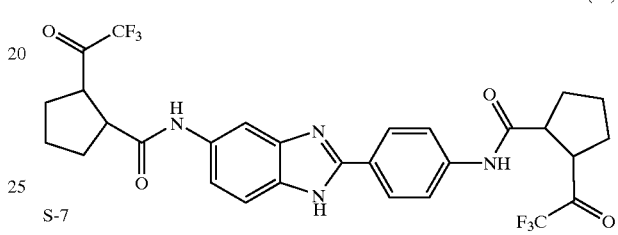

S-7

(10) Bis-(N-trifluoroacetylproline) benzimidazole was prepared by method A except that CH$_2$Cl$_2$ used as solvent from 2-(4-aminophenyl)-6-amino benzimidazole (0.448 mg, 2.0 mmole) and (s)-(−)-N-trifluoroacetylproline chloride (42.0 ml, 0.1 M in CH$_2$Cl$_2$). The resulting solid was purified on silica gel (5% MeOH in CH$_2$Cl$_2$). HPLC showed the product was 98.5% pure.

(11)

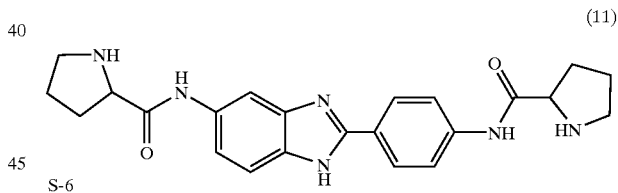

S-6

(11) Bis-proline benzimidazole was synthesized by dissolving the bis-trifluoroacetyl derivative in MeOH (5 ml) to which was added a LiOH solution (0.210 g in 5 ml water). The above mixture was heated to 42° C. for 2 hours. The reaction mixture was extracted with CH$_2$Cl$_2$ (5×15 ml). The combined organic extracts were concentrated under vacuum to give a solid which was 95.6% pure by HPLC.

(12)

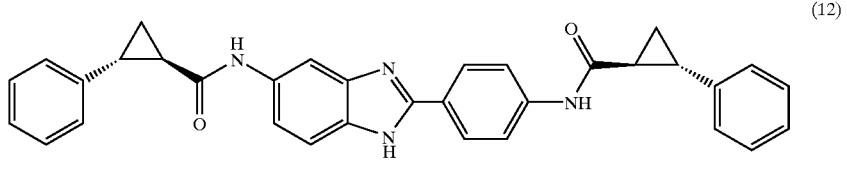

S-8

(12) Bis-trans-2-phenyl-cyclopropanecarbonyl benzimidazole was prepared by method C from 2-(4-aminophenyl)-6-amino benzimidazole (0.500 g, 2.23 mmole) and trans-2-phenyl-cyclopropanecarbonyl chloride (0.831 ml, 0.966 g, 5.35 mmole). The resulting solid was purified on silica gel (5% MeOH in CH₂Cl₂). HPLC showed the product was 95.5% pure.

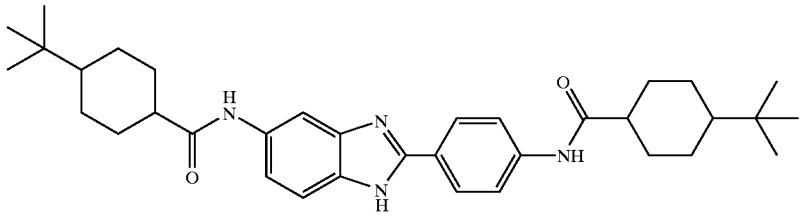

(13)

S-9

(13) Bis-4-t-butylcyclohexyl carbonyl benzimidazole was prepared by method C from 2-(4-aminophenyl)-6-amino benzimidazole (0.425 g, 1.89 mmole) and 4-t-butyl cyclohexylcarbonyl chloride (0.814 g, 4.25 mmole). The resulting solid was purified on silica gel (5% MeOH in CH₂Cl₂). HPLC showed the product was 90% pure.

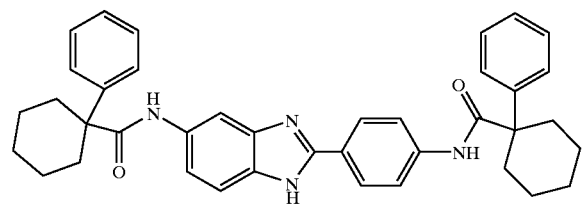

(14)

S-10

(14) Bis-1-phenylcyclohexyl carbonyl benzimidazole was prepared by method C from 2-(4-aminophenyl)-6-amino benzimidazole (0.467 g, 2.08 mmole) and 1-phenyl-cyclohexylcarbonyl chloride (1.046 g). The resulting solid was purified on silica gel (5% MeOH in CH₂Cl₂). HPLC showed the product was 93.3% pure.

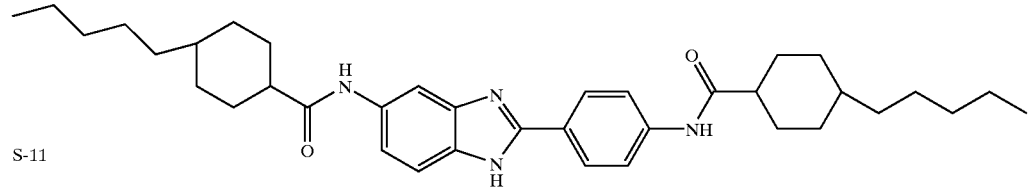

(15)

S-11

(15) Bis-trans-4-pentylcyclohexylcarbonyl benzimidazole was synthesized as follows: oxalyl chloride (1.07 ml, 2 M in CH₂Cl₂) was added to trans-4-pentylcyclohexyl carboxylic acid (0.424 g, 2.14 mmole) followed by one drop DMF. The mixture was allowed to react at RT for 1 hour. To the above solution was added 2-(4-aminophenyl)-6-aminobenzimidazole (0.200 g, 0.89 mmole) in pyridine (2 ml). The reaction was heated to 60° C. overnight. The reaction was cooled and the precipitate filtered and washed with NaHCO₃

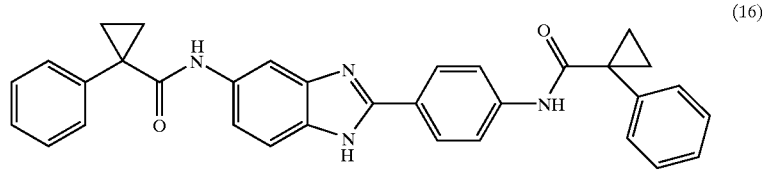

(16)

S-12

(16) Bis-1-phenylcyclopropane carbonyl benzimidazole was prepared by method C from 2-(4-aminophenyl)-6-amino benzimidazole (0.530 g, 2.36 μmmole) and 1-phenyl-cyclopropanecarbonyl chloride (0.9625 g, 5.3 mmole). The resulting solid was purified on silica gel (5% MeOH in $CH_2Cl_2$). HPLC showed the product was 93.4% pure.

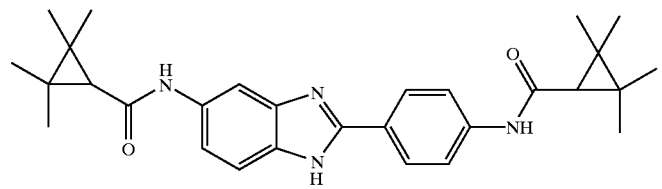

(17)

S-55

(17) Bis-(2,2,3,3-tetramethylcyclopropane) carbonyl benzimidazole was synthesized as follows: oxalyl chloride (1.07 ml, 2 M in $CH_2Cl_2$) was added to 2,2,3,3-tetramethylcyclopropane carboxylic acid (0.305 g, 2.14 mmole) followed by one drop DMF. The mixture was allowed to react at RT for 1 hour. To the above solution was added 2-(4-aminophenyl)-6-amino benzimidazole (0.200 g, 0.89 mmole) in pyridine (2 ml). The reaction was heated to 60° C. overnight. The reaction was cooled and the precipitate filtered and washed with $NaHCO_3$ and hexanes. The resulting solid was purified by preparative HPLC to yield a solid that was >99% pure.

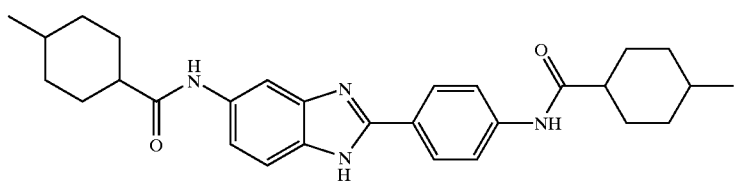

(18)

S-54

(18) Bis-4-methylcyclohexyl carbonyl benzimidazole was prepared by method D from 2-(4-aminophenyl)-6-amino benzimidazole (0.100 g, 0.44 mmole) and 4-methylcyclohexylcarboxylic acid (0.138 g, 0.96 mmole). The resulting solid was purified on silica gel (5% MeOH in $CH_2Cl_2$). HPLC showed the product was 94.5% pure.

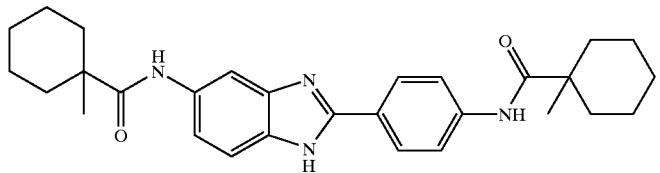

(19)

S-58

(19) Bis-1-methylcyclohexyl carbonyl benzimidazole was synthesized as follows: oxalyl chloride (1.07 ml, 2 M in $CH_2Cl_2$) was added to 1-methyl-cyclohexane carboxylic acid (0.305 g, 2.14 mmole) followed by one drop DMF. The mixture was allowed to react at RT for 1 hour. To the above solution was added 2-(4-aminophenyl)-6-amino-benzimidazole (0.200 g, 0.89 mmole) in pyridine (2 ml). The reaction mixture was heated to 60° C. overnight. The reaction was cooled and the precipitate filtered and washed with $NaHCO_3$ and hexanes. The resulting solid was purified by preparative HPLC to give a solid that was >99% pure.

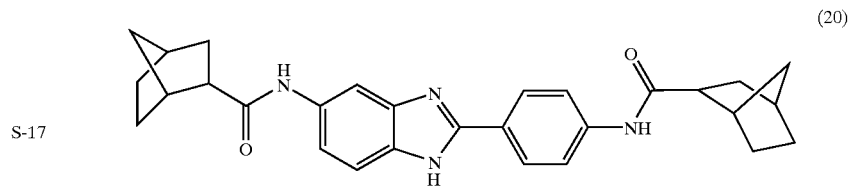

(20)

S-17

(20) Bis-bicyclo[2:2:1]heptane-2-carbonyl benzimidazole was prepared as follows: oxalyl chloride (1.07 ml, 2 M in $CH_2Cl_2$) was added to bicyclo[2.2.1]heptane carboxylic acid (0.305 g, 2.14 mmole) followed by one drop DMF. The mixture was allowed to react at RT for 1.0 hour. To the above solution was added 2-(4-aminophenyl)-6-amino-benzimidazole (0.200 g, 0.89 mmole) in pyridine (2 ml). The reaction was heated to 60° C. overnight. The reaction was cooled and the precipitate filtered and washed with $NaHCO_3$ and hexanes. The resulting solid was purified by preparative HPLC to give a solid that was 68% pure.

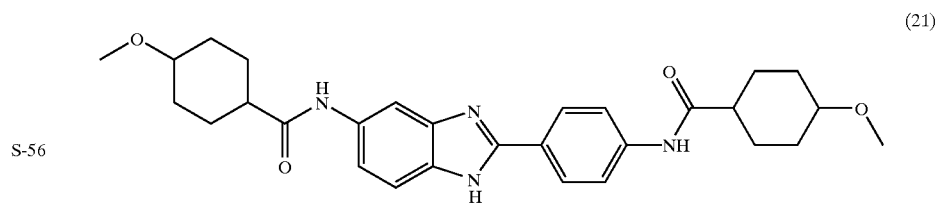

(21)

S-56

(21) Bis-4-methoxyclohexyl carbonyl benzimidazole was synthesized as follows: Oxalyl chloride, (1.07. ml, 2 M in $CH_2Cl_2$) was added to 4-methoxy-cyclohexane carboxylic acid (0.338 g, 2.14 mmole) followed by one drop DMF. The mixture was allowed to react at RT for 1.0 hour. To the above solution was added 2-(4-aminophenyl)-6-amino-benzimidazole (0.200 g, 0.89 mmole) in pyridine (2 ml). The reaction was heated to 60° C. overnight. The reaction was cooled and the precipitate filtered and washed with $NaHCO_3$ and hexanes.

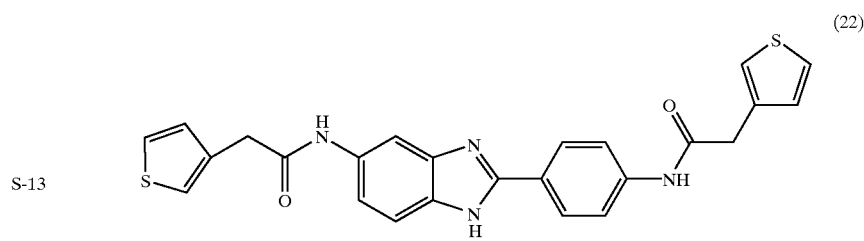

(22)

S-13

(22) Bis-3-thiopheneacetyl benzimidazole was produced as follows: Oxalyl chloride (1.07 ml, 2 M in CH$_2$Cl$_2$) was added to 3-thiopheneacetic acid (0.338 g, 2.14 mmole) followed by one drop DMF. The mixture was allowed to react at RT for 1.0 hour. To the above solution was added 2-(4-aminophenyl)-6-amino-benzimidazole (0.200 g, 0.89 mmole) in pyridine (2 ml). The reaction was heated to 60° C. overnight. The reaction was cooled and the precipitate filtered and washed with NaHCO$_3$ and hexanes.

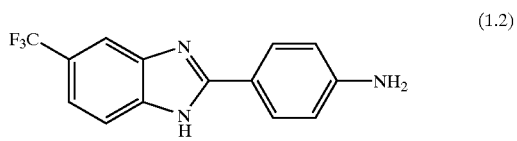

(23)

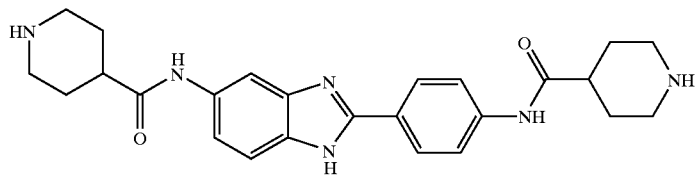

S-14

(23) Bis-4-nipecotamide benzimidazole was produced as follows: Bis-N-Boc-4-nipecotamide benzimidazole (0.400 g) was dissolved in 1:1 TFA-CH$_2$Cl$_2$ (4 ml) at 20° C. overnight. The solvent was removed under vacuum and water added, frozen on dry ice and lyophilized to dryness. The Boc-protected benzimidazole was synthesized as follows: Oxalyl chloride (2.82 ml, 2 M in CH$_2$Cl$_2$) was added to N-Boc-nipecotic acid (1.293 g, 5.64 mmole) followed by one drop DMF. The mixture was allowed to react at RT for 1 hour. To the above solution was added. 2-(4-aminophenyl)-6-amino-benzimidazole (0.500 g, 2.24 mmole) in pyridine (5 ml). The reaction was heated to 60° C. overnight. The reaction was cooled and the precipitate filtered and washed with NaHCO$_3$ and hexanes. The resulting solid was found to be >99% pure by HPLC.

Monoamido-phenylbenzimidazole Inhibitors of IgE

A family of IgE inhibitors related to the diamido-phenylbenzimidazole compounds described above are asymmetrical monoamido-phenylbenzimidazole compounds. Several monoamido variations were synthesized. The syntheses of several of these species are provided below.

The first species, 2-(N-Cyclohexanecarbonyl-4-aminophenyl)-5 trifluoromethyl benzimidazole, designated as (1), was synthesized from the following series of benzimidazole intermediates: 1) 2-(4-nitrophenyl)-5-trifluoromethyl benzimidazole (designated 1.1 and 2) 2-(4-aminophenyl)-5-trifluoromethyl benzimidazole (designated 1.2).

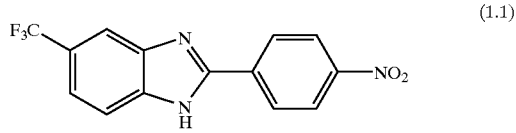

(1.1) 2-(4-Nitrophenyl)-5-trifluoromethyl benzimidazole was synthesized as follows: 1,2-diamino-4-trifluoromethylbenzene (1.76 g, 10.0 mmole) was mixed with 4-nitrobenzoic acid (1.67 g, 9.8 mmole), dissolved in POCl$_3$ (12 ml), and heated to reflux for 2.5 hours. The reaction mixture was cooled and cautiously poured onto ice. The resulting solid was filtered, washed with NaHCO$_3$ and used without further purification.

(1.2) 2-(4-Aminophenyl)-5-trifluoromethyl benzimidazole was produced from 2-(4-nitrophenyl)-5-trifluoromethyl benzimidazole (1.1; see above). The crude 2-(4-nitrophenyl)-5-trifluoromethyl benzimidazole filtrate was dissolved in conc. HCl (15 ml) to which was added SnCl$_2$·H$_2$O (13.5 g, 59 mmol) and heated to reflux for 16 h. The reaction was cooled and the HCl salt precipitated by the addition of EtOH (75 ml). The solid was filtered, washed with ethanol, and dissolved in water. The salt was neutralized by the addition of conc. ammonium hydroxide and the free base isolated by filtration. The product was characterized by mass spectroscopy.

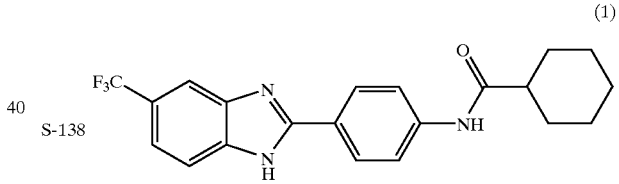

S-138

(1) 2-(N-Cyclohexanecarbonyl-4-aminophenyl)-5-trifluoromethyl benzimidazole was prepared from the amine, 2-(4-aminophenyl)-5-trifluoromethyl benzimidazole (1.2 see above). The amine (0.239 g, 0.86-mmol) was dissolved in THF:H$_2$O (5 ml, 1:1) followed by K$_2$CO$_3$ (0.1213 g, 0.88 mmol) and cyclohexyl carbonyl chloride (130 µL, 0.95 mmol). The reaction mixture was shaken for 23 h at room temperature. Sodium chloride was added to the reaction and the mixture extracted with EtOAc. The combined organic extracts were washed with water, dried over Na$_2$SO$_4$ and concentrated under vacuum. The resulting solid was purified by preparative TLC (10% MeOH in CH$_2$Cl$_2$).

The next species (2), 2-(N-cyclohexanecarbonyl-4-aminophenyl)-5-fluoro benzimidazole, was synthesized from the following series of benzimidazole intermediates: 1) 2-(4-nitrophenyl)-5-fluoro benzimidazole (designated 2.1) and 2) 2-(4-aminophenyl)-5-fluoro benzimidazole (designated 2.2).

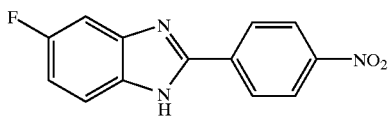
(2.1)

(2.1) 2-(4-Nitrophenyl)-5-fluoro benzimidazole was synthesized as follows: 1,2-diamino-4-fluorobenzene (1.26 g, 10.0 mmole) was mixed with 4-nitrobenzoic acid (1.67 g, 9.8 mmole) and dissolved in POCl₃ (10 ml) and heated to reflux for 2.5 hours. The reaction mixture was cooled and cautiously poured onto ice. The resulting solid was filtered, washed with NaHCO₃ and used without further purification.

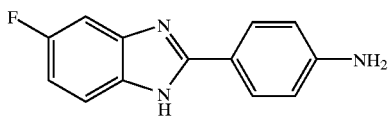
(2.2)

(2.2) 2-(4-Aminophenyl)-5-fluoro benzimidazole was prepared by dissolving 1.0 g of the above nitrobenzimidazole (2.1) in 30% Na₂S·9H₂O (20 ml) with stirring at RT for 24 h. The reaction mixture was diluted with water and extracted with EtOAc. The combined organic extracts were dried over sodium sulfate and concentrated under vacuum. The product was characterized by mass spectroscopy.

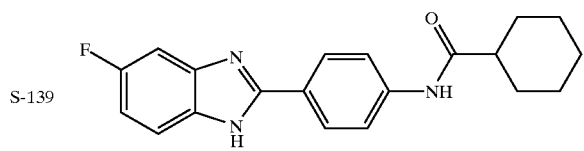
(2)

(2) 2-(N-Cyclohexanecarbonyl-4-aminophenyl)-5-fluoro benzimidazole was prepared by dissolving 0.100 g (0.44 mmol) of the above amine (2.2) in pyridine (1.0 ml) followed by cyclohexanecarbonyl chloride (63.2 μl) and heated to 60° C. overnight. The reaction was diluted with water (8 ml) and extracted with EtOAc. The combined organic fractions were dried (Na₂SO₄) and concentrated under vacuum. The resulting solid was purified by flash chromatography (5% MeOH—CH₂Cl₂).

The next species (3), 2-(N-3',4'-dichlorobenzoyl-4-aminophenyl)-3,4-dimethyl benzimidazole, was synthesized from the following series of benzimidazole intermediates: 1) 2-(4-nitrophenyl)-4,5-dimethyl benzimidazole (designated 3.1) and 2) 2-(4-aminophenyl)-4,5-dimethyl benzimidazole (designated 3.2).

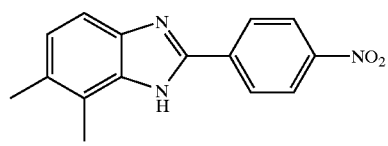
(3.1)

(3.1) 2-(4-Nitrophenyl)-4,5-dimethyl benzimidazole was prepared by mixing 1,2-diamino-3,4-dimethylbenzene (1.36 g, 9.8 mmole) with 4-nitrobenzoic acid (1.67 g, 9.8 mmole) and dissolved in POCl₃ (10 ml) and heated to reflux for 2.5 hours. The reaction mixture was cooled and cautiously poured onto ice. The resulting solid was filtered, washed with NaHCO₃ and used without further purification.

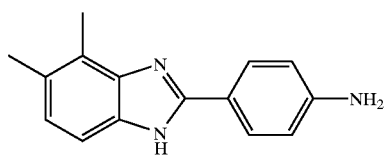
(3.2)

(3.2) 2-(4-Aminophenyl)-4,5-dimethyl benzimidazole was synthesized by dissolving 1.0 g of the above nitrobenzimidazole (3.1) in 30% Na₂S·9H₂O (20 ml) and stirring at RT for 2.5 h. The reaction mixture was diluted with water and extracted with EtOAc. The combined organic extracts were dried over sodium sulfate and concentrated under vacuum. The product was characterized by mass spectroscopy.

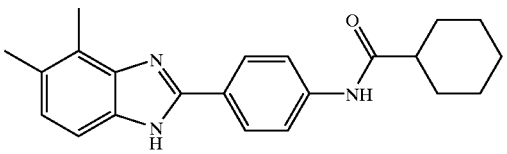
(3)

(3) 2-(N-Cyclohexanecarbonyl-4-aminophenyl)-3,4-dimethyl benzimidazole was prepared by dissolving 0.0954 g (0.402 mmol) of the above amine (3.2) in 1.0 ml of pyridine followed by cyclohexanecarbonyl chloride (57.6 μl) and heated to 60° C. overnight. The reaction was diluted with water (8 ml) and extracted with EtOAc. The combined organic fractions were dried (Na₂SO₄) and concentrated under vacuum. The resulting solid was purified by flash chromatography (5% MeOH/CH₂Cl₂).

Diamido-phenylbenzimidazole Species

The diamido-phenylbenzimidazole inhibitors of IgE in accordance with various embodiments are represented by the generic formula:

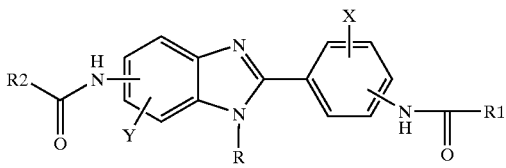
Genus (A)

wherein X and Y are independently selected from the group consisting of mono, di, tri, and tetra substituted H, alkyl, alkoxy, aryl, substituted aryl, hydroxy, halogen, amino, alkylamino, nitro, cyano, CF₃, OCF₃, CONH₂, CONHR, and NHCOR1;

wherein R is selected from the group consisting of H, CH₃, C₂H₅, C₃H₇, C₄H₉, CH₂Ph, and CH₂C₆H₄—F(p-);

wherein R1 and R2 are independently selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings, and substituted heterocyclic rings;

wherein R1 and R2 cannot both be methyl groups;

wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl and substituted heterocyclic rings are selected from the group consisting of alkyl, acyl, aryl, $CF_3$, $CH_3$, $OCH_3$, OH, CN, $COOR_5$, COOH, $COCF_3$, and heterocyclic rings; and wherein at least one of R1, R2 or said substituents is a heterocyclic ring.

The following species, encompassed within the disclosed generic formulae, were synthesized and tested for their ability to regulate IgE. These species are presented below:

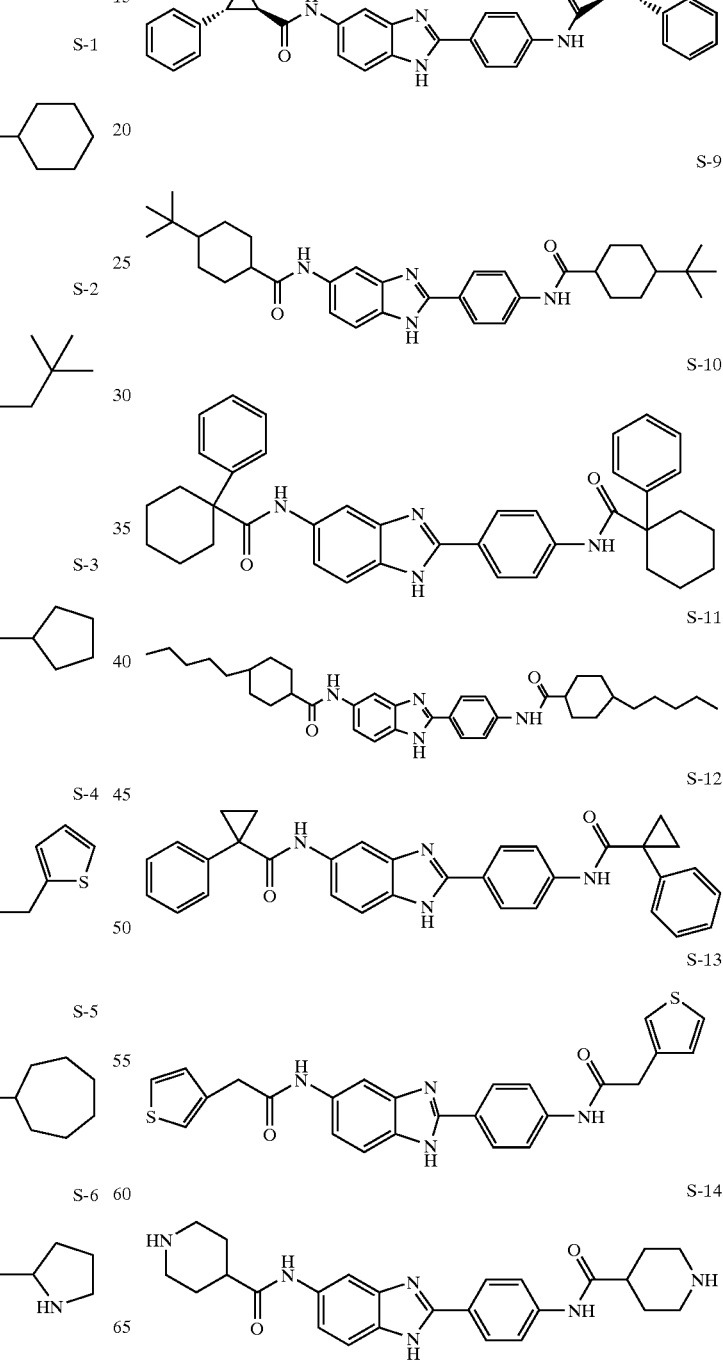

S-15
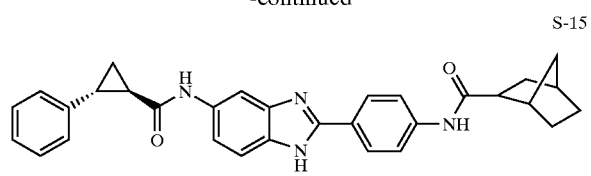
S-16
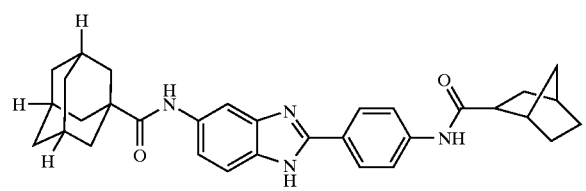
S-17
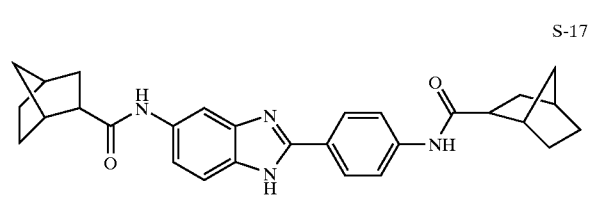
S-18
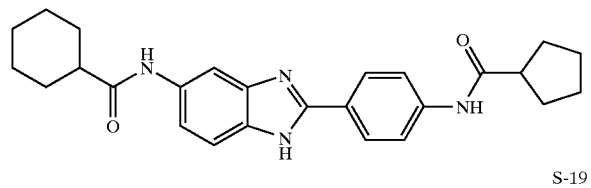
S-19
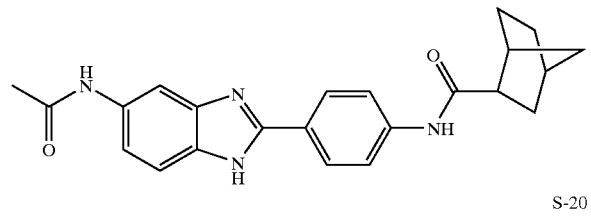
S-20
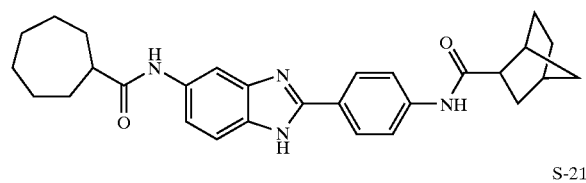
S-21
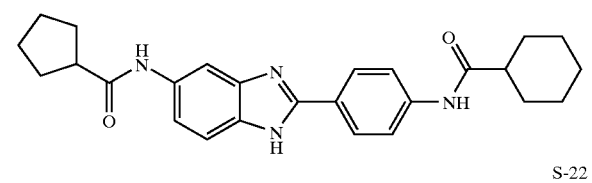
S-22
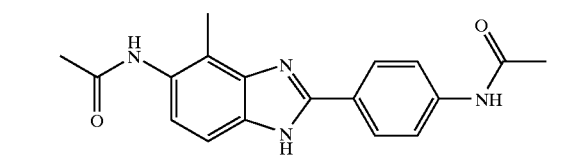
S-23
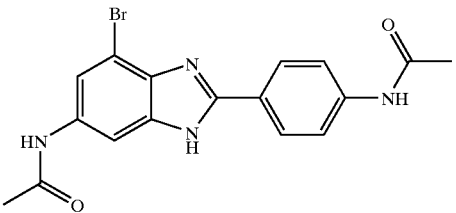
S-24
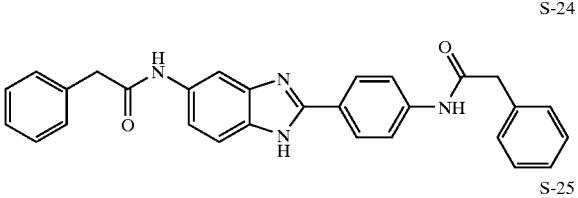
S-25
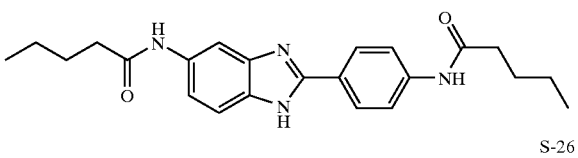
S-26
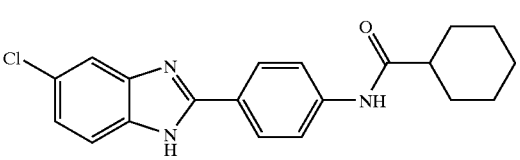
S-27
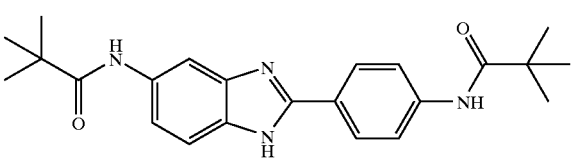
S-28
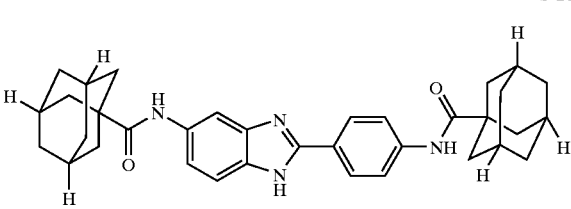
S-29
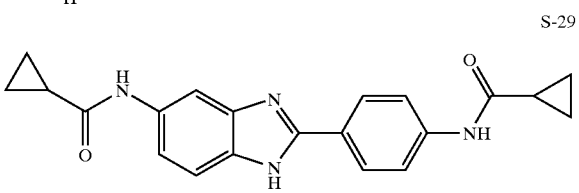
S-30
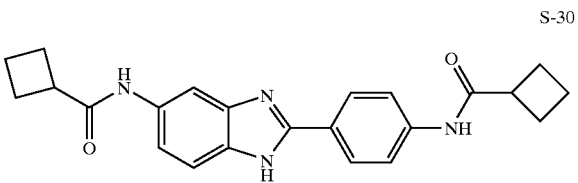
S-31

-continued
S-32
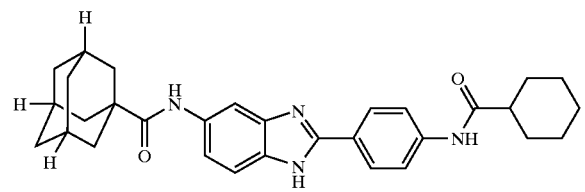
S-33
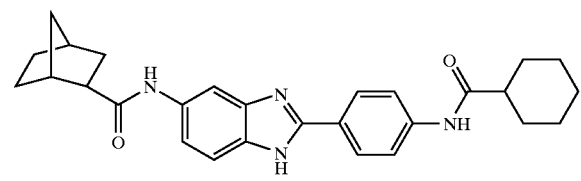
S-34
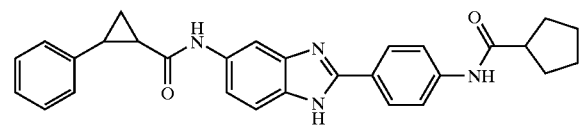
S-35
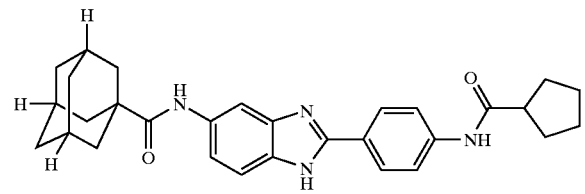
S-36
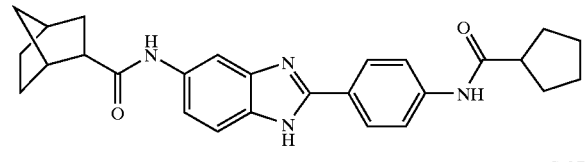
S-37
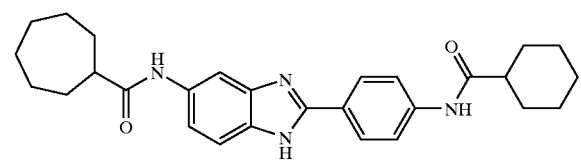
S-38
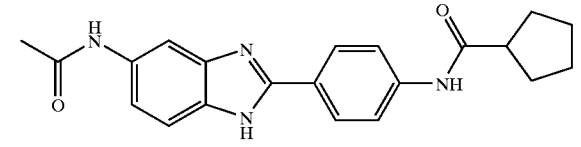
-continued
S-39
S-40
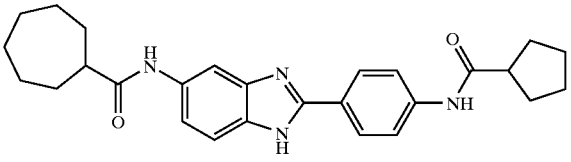
S-41
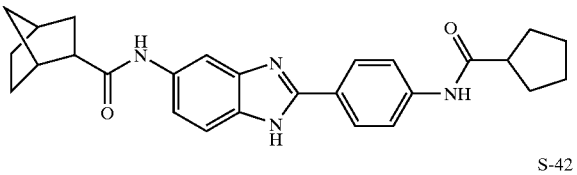
S-42
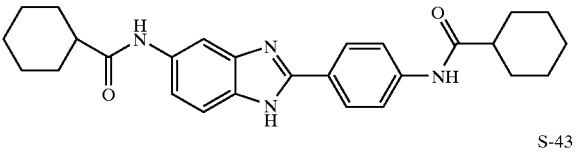
S-43
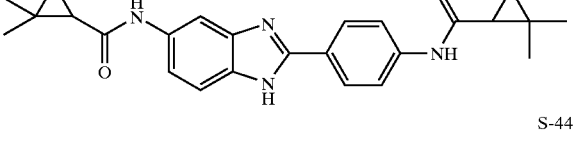
S-44
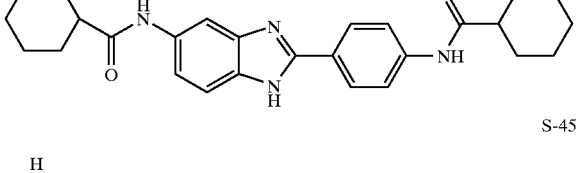
S-45
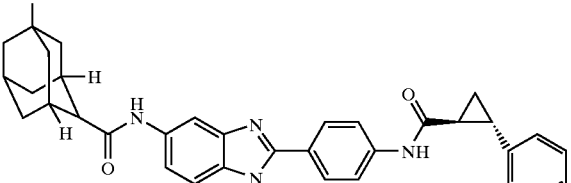
S-46
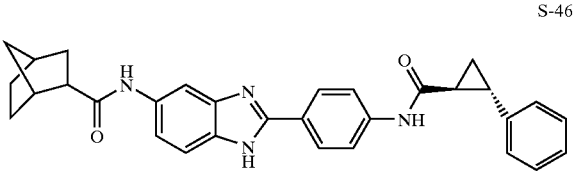
S-47
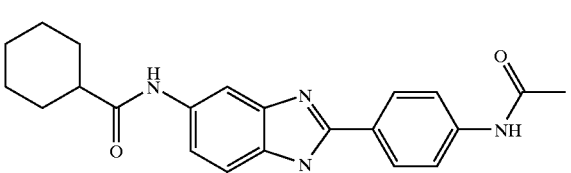
S-48
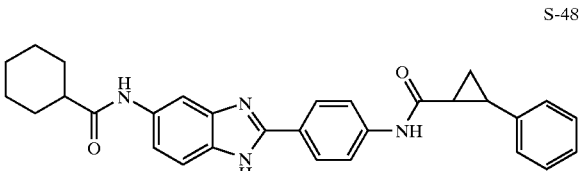

-continued
S-49
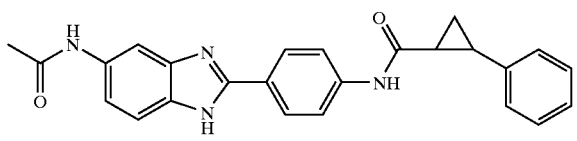
S-50
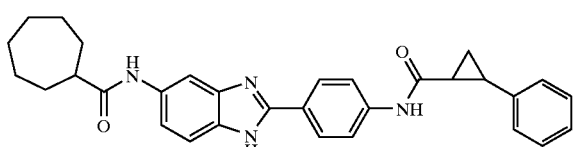
S-51
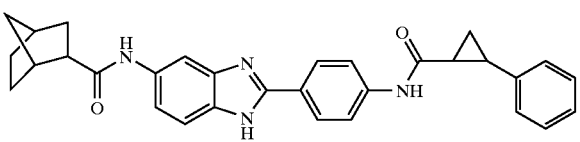
S-52
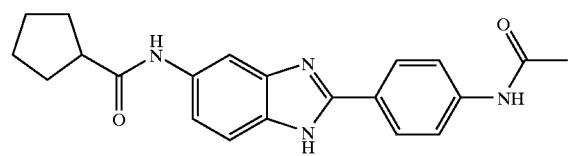
S-53
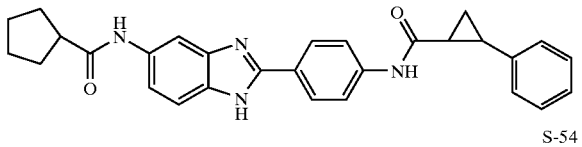
S-54
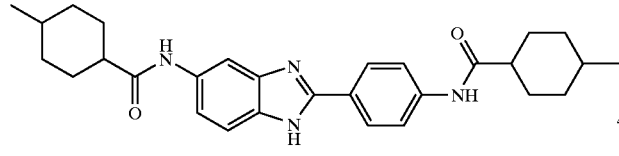
S-55
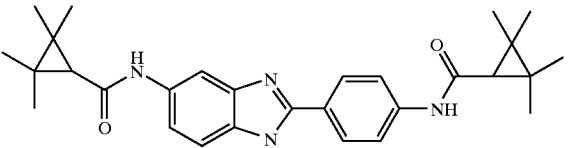
S-56
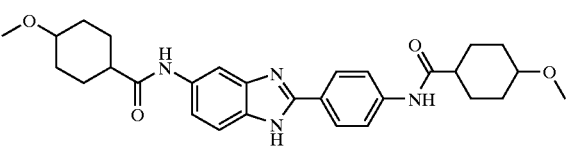
S-57
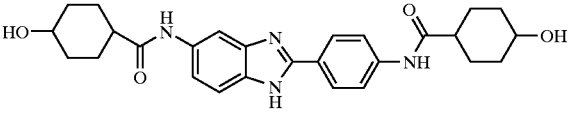
-continued
S-58
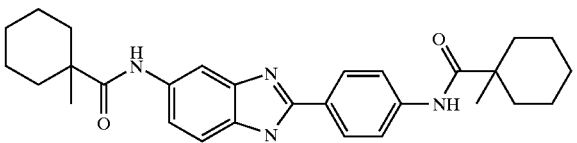
S-60
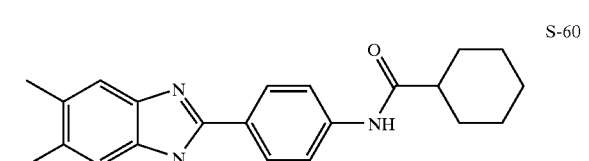
S-61
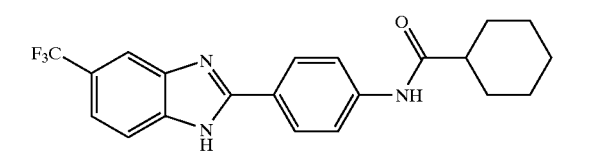
S-62
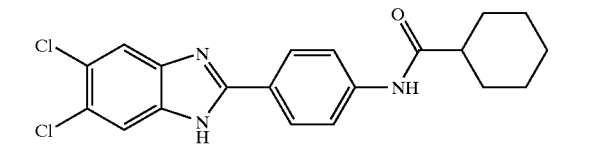
S-63
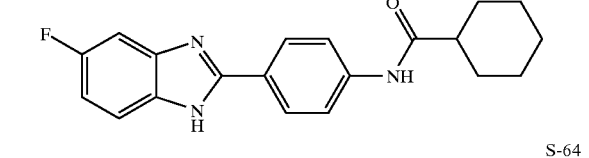
S-64
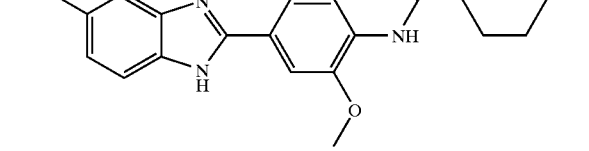
S-65
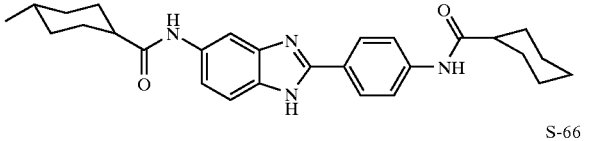
S-66
S-67
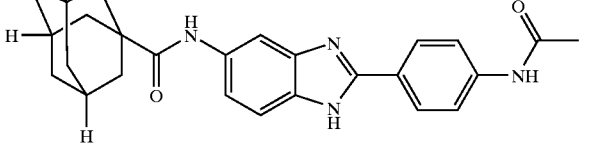

S-68
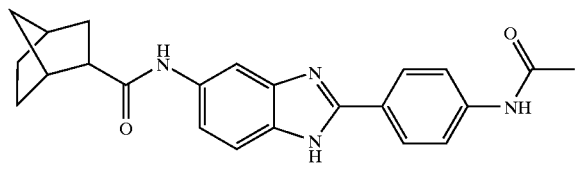
S-76
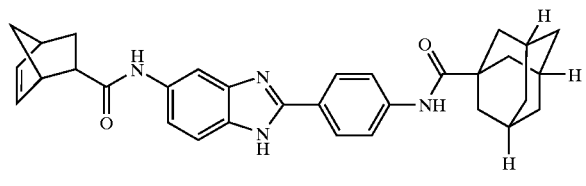
S-69
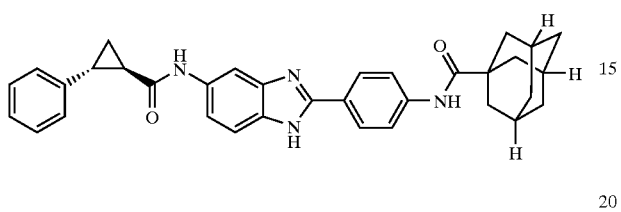
S-77
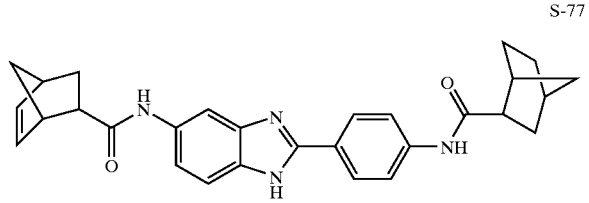
S-70
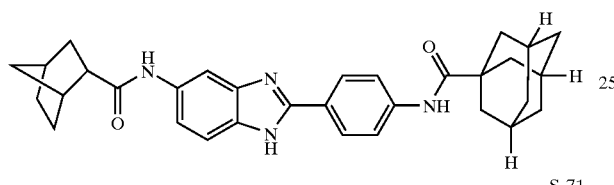
S-78
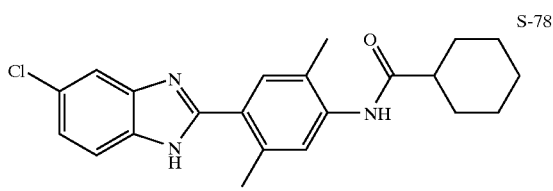
S-71
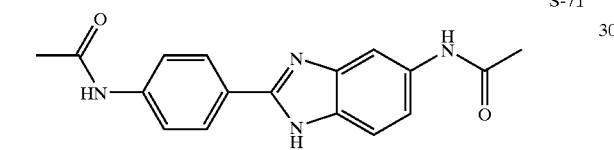
S-79
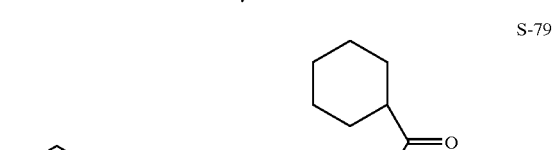
S-72
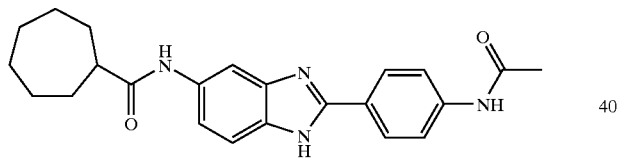
S-80
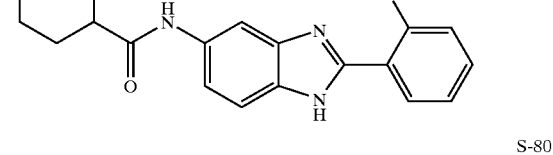
S-73
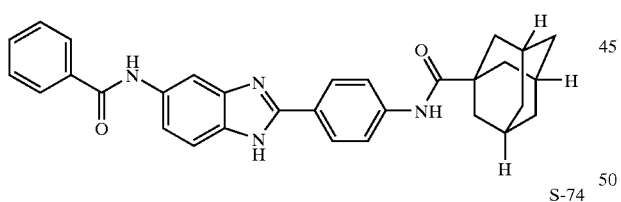
S-81
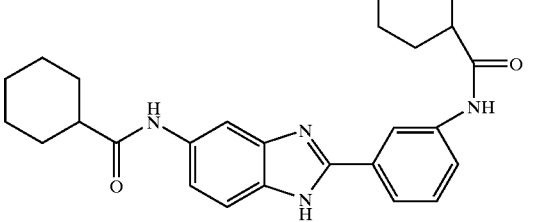
S-74
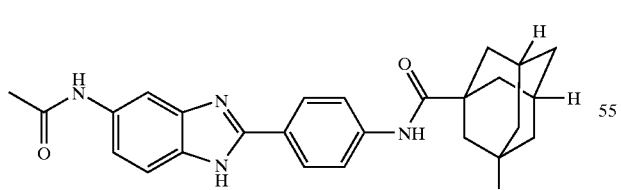
S-75
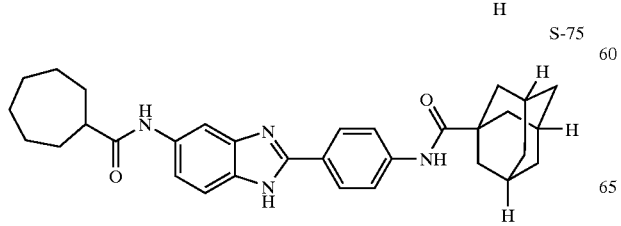

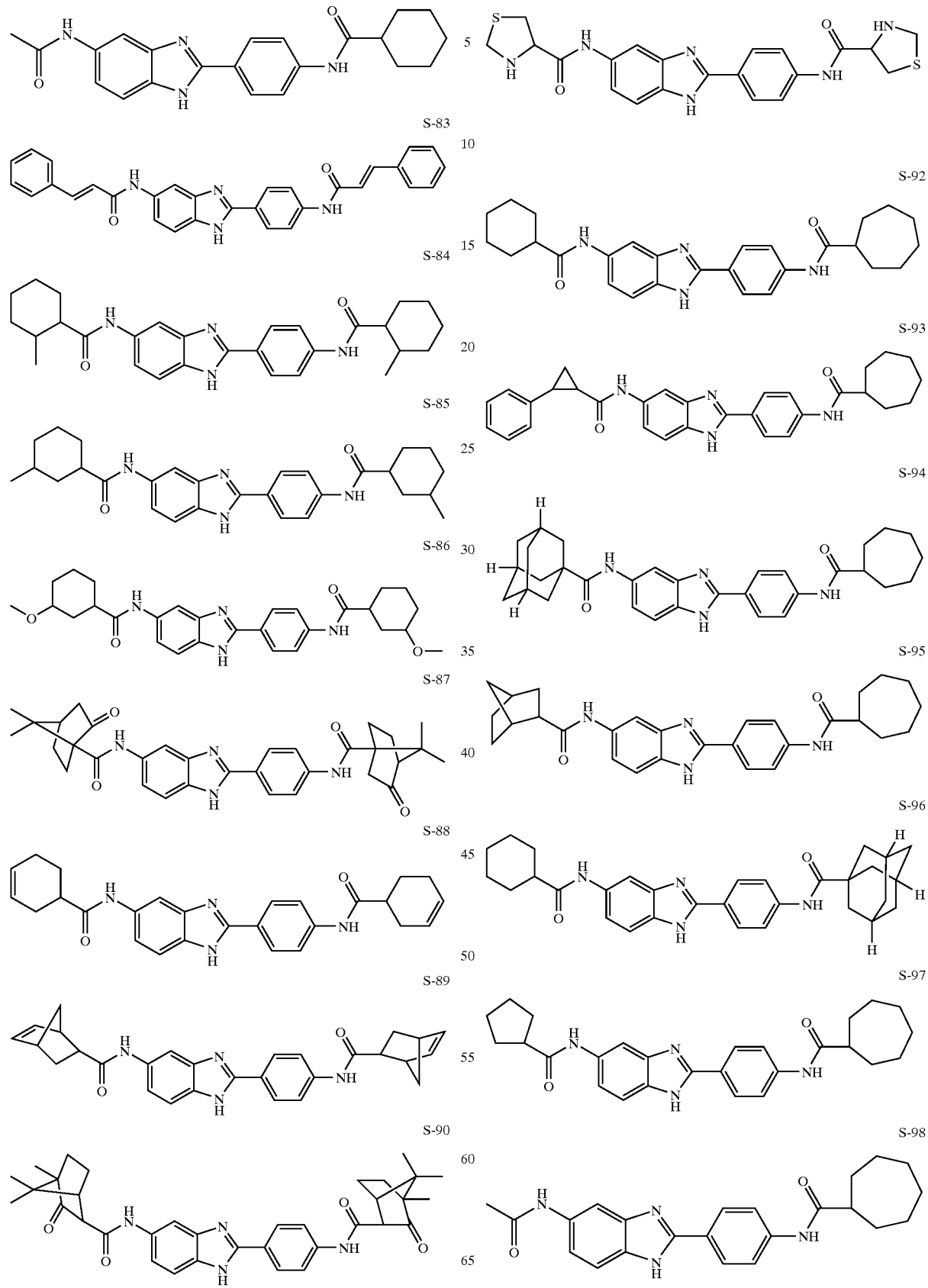

S-99
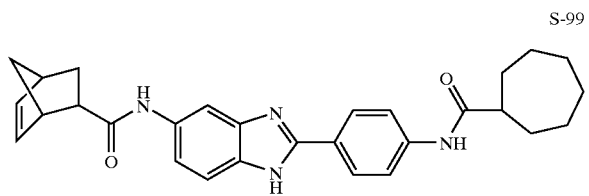

S-107
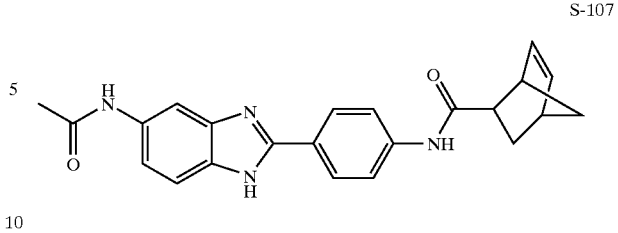

S-100
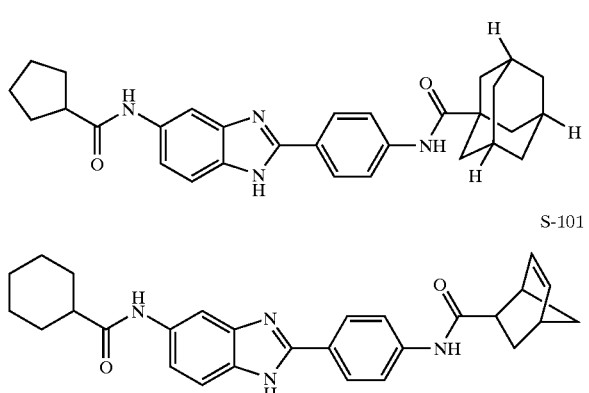

S-108
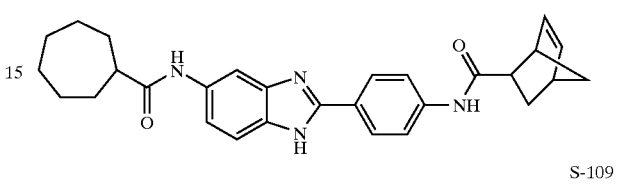

S-101

S-109
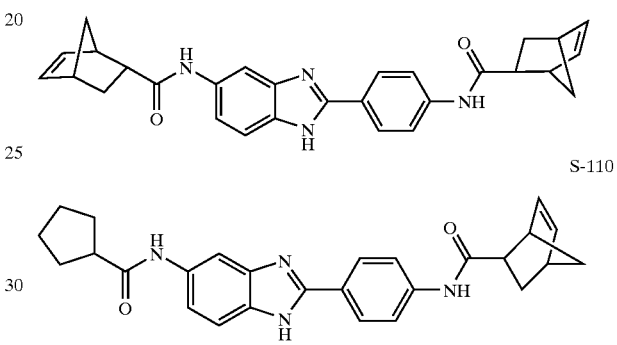

S-102

S-110

S-103
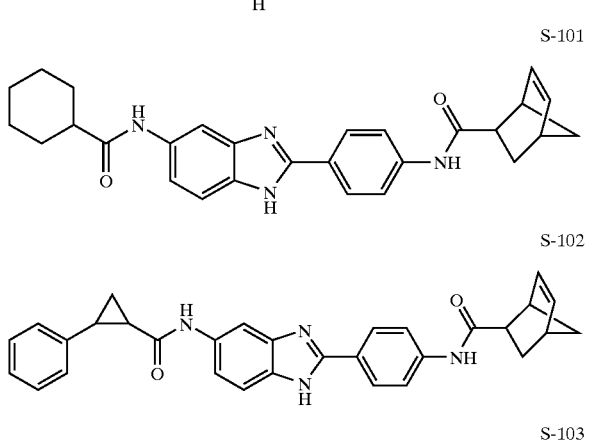

S-104

S-105

S-106
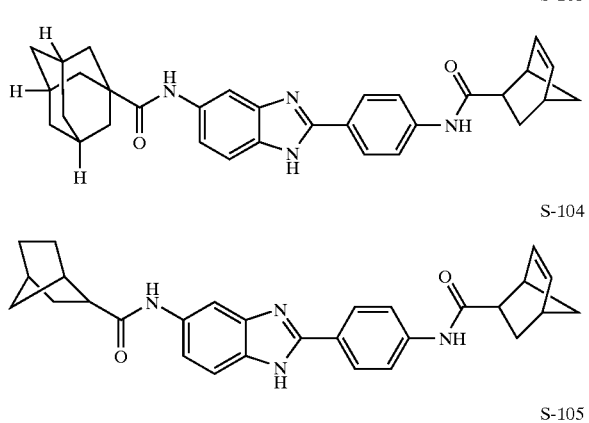
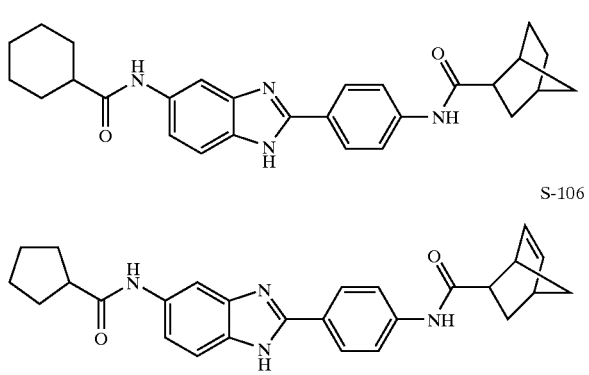

Monoamido-phenylbenzimidazole Species

The monoamido-phenylbenzimidazole inhibitors of IgE in accordance with various embodiments are represented by the generic formula:

Genus (B)
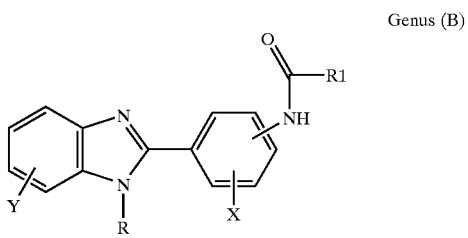

wherein X is selected from the group consisting of mono, di, tri, and tetra substituted H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2CH_4$—F(p-);

wherein Y is selected from the group consisting of mono, di, tri, and tetra substituted H, alkyl, alkoxy, aryl, benzo, substituted aryl, hydroxy, halogen, amino, alkylamino, nitro, cyano, $CF_3$, $OCF_3$, COPh, $COOCH_3$, $CONH_2$, CONHR, NHCONHR1, and NHCOR1; and wherein R1 is selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings containing one or more heteroatoms, and substituted heterocyclic rings; and wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl, and substituted heterocyclic rings are selected from the group consisting of alkyl, aryl, $CF_3$, $CH_3$, $OCH_3$, OH, CN, $COOR_5$, COOH, and heterocyclic rings.

Several species of asymmetrical monoamido-phenylbenzimidazole compounds were also effective in regulating IgE. These species have the following formulae:

S-111
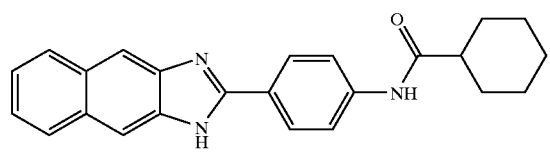

S-112
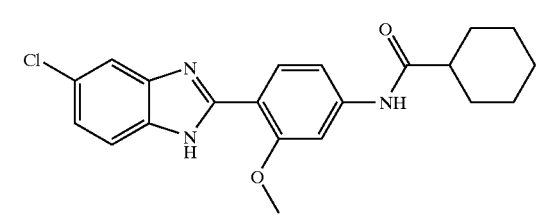

S-113
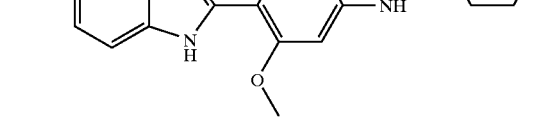

S-114
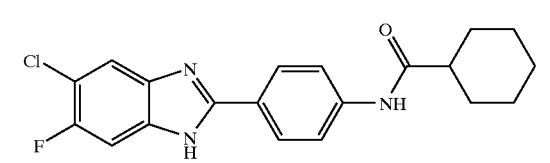

S-115
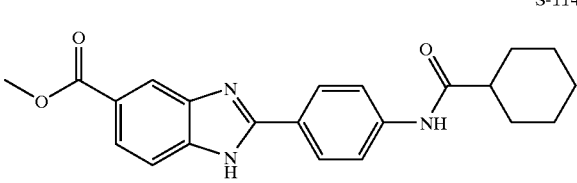

S-116
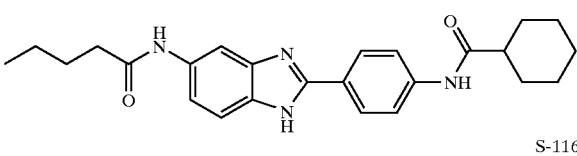

S-117
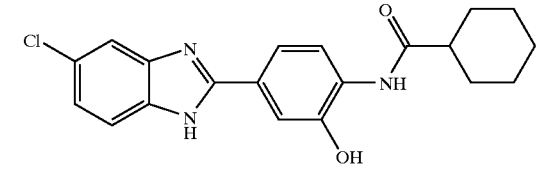

-continued

S-118
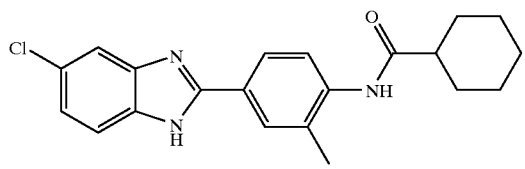

S-119
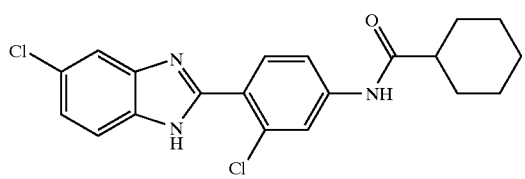

S-120
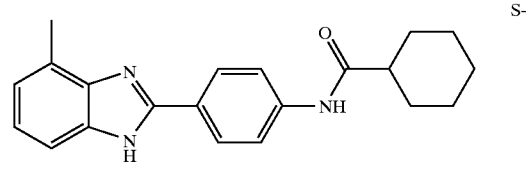

S-121
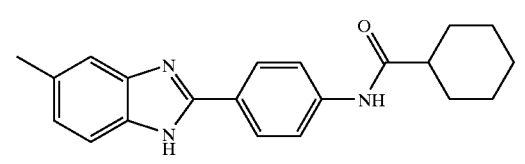

S-122
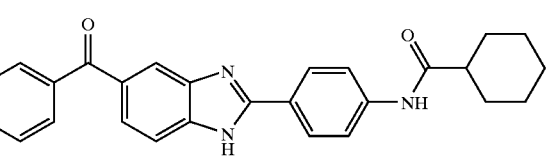

S-123

Suppressions of IgE Response

The inhibitory activity of the small molecules of the preferred embodiments were assayed using both the ex vivo and in vivo assays as described above. All of the compounds presented above were active in suppressing the IgE response. In the ex vivo assay, compounds produced 50% inhibition at concentrations ranging from 1 pM to 10 μM. In the in vivo assay, the compounds were effective at concentrations ranging from less than about 0.01 mg/kg/day to about 25 mg/kg/day, when administered in divided doses (e.g., two to four times daily) for at least two to seven consecutive days. The diamido-phenylbenzimidazole compounds were generally more potent than the monoamido compounds. Thus, the small molecule inhibitors of the preferred embodiments are disclosed as being useful in lowering the antigen-induced increase in IgE concentration, and consequently, in the treatment of IgE-dependent processes such as allergies in general and allergic asthma in particular.

Treatment Regimens

The amount of the IgE inhibitor compound which may be effective in treating a particular allergy or condition will depend on the nature of the disorder, and can be determined by standard clinical techniques. The precise dose to be employed in a given situation will also depend on the choice of compound and the seriousness of the condition, and should be decided according to the judgement of the practitioner and each patient's circumstances. Appropriate dosages can be determined and adjusted by the practitioner based on dose response relationships between the patient's IgE levels as well as standard indices of pulmonary and hemodynamic changes. Moreover, those skilled in the art will appreciate that dose ranges can be determined without undue experimentation by following the protocol(s) disclosed herein for ex vivo and in vivo screening (See for example Hasegawa et al., *J. Med. Chem.* 40: 395–407 (1997and Ohmori et al., *Int. J Immunopharmacol.* 15:573–579 (1993); employing similar ex vivo and in vivo assays for determining dose-response relationships for IgE suppression by naphthalene derivatives; incorporated herein by reference).

Initially, suitable dosages of the compounds will generally range from about 0.001 mg to about 300 mg per kg body weight per day in divided doses, more preferably, between about 0.01 mg and 100 mg per kg body weight per day in divided doses. The compounds are preferably administered systemically as pharmaceutical formulations appropriate to such routes as oral, aerosol, intravenous, subcutaneously, or by any other route which may be effective in providing systemic dosing of the active compound. The compositions of pharmaceutical formulations are well known in the art. The treatment regimen preferably involves periodic administration. Moreover, long-term therapy may be indicated where allergic reactions appear to be triggered by continuous exposure to the allergen(s). Daily or twice daily administration has been effective in suppressing the IgE response to a single antigen challenge in animals when carried out continuously from a period of two to seven consecutive days. Thus, in a preferred embodiment the compound is administered for at least two consecutive days at regular periodic intervals. However, the treatment regimen, including frequency of dosing and duration of treatment may be determined by the skilled practitioner, and modified as needed to provide optimal IgE down-regulation, depending on nature of the allergen, the dose, frequency, and duration of the allergen exposure, and the standard clinical indices.

In a certain embodiment, an IgE-suppressing compound may be administered in conjunction with one or more of the other small molecule inhibitors disclosed, in order to produce optimal down-regulation of the patient's IgE response. Further, it is envisioned that one or more of the compounds of the preferred embodiments may be administered in combination with other drugs already known or later discovered for treatment of the underlying cause as well as the acute symptoms of allergy or asthma. Such combination therapies envisioned within the scope of the preferred embodiments include mixing of one or more of the small molecule IgE-inhibitors together with one or more additional ingredients, known to be effective in reducing at least one symptom of the disease condition. In a variation, the small molecule IgE-inhibitors herein disclosed may be administered separately from the additional drugs, but during the same course of the disease condition, wherein both the IgE-inhibitor(s) and the palliative compounds are administered in accordance with their independent effective treatment regimens.

While a number of preferred embodiments and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A pharmaceutical composition for treating an allergic reaction associated with increased IgE levels in a mammal in need thereof comprising one or more of the following compounds selected from Genus A or Genus B:

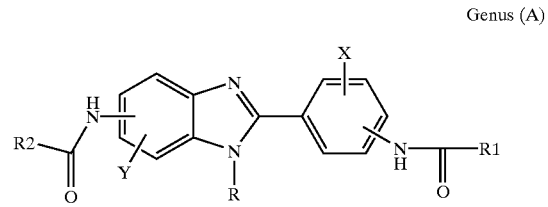

Genus (A)

wherein X and Y are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2C_6H_4$—F (p-);

wherein R1 and R2 are independently selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings, and substituted heterocyclic rings;

wherein R1 and R2 cannot both be methyl groups;

wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl and substituted heterocyclic rings are selected from the group consisting of alkyl, acyl, aryl, $CF_3$, $CH_3$, $OCH_3$, OH, CN, COOR, COOH, $COCF_3$, and heterocyclic rings; and wherein at least one of R1, R2 or said substituents is a heterocyclic ring; and

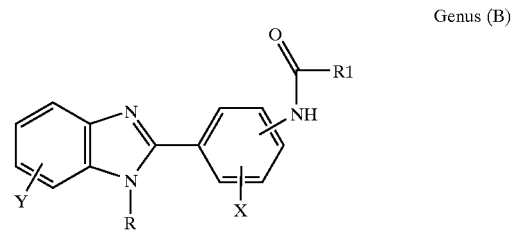

Genus (B)

wherein X is selected from the group consisting of mono, di, tri, and tetra substituted H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2C_6H_4$—F (p-);

wherein Y is selected from the group consisting of mono, di, tri, and tetra substituted H, alkyl, alkoxy, aryl, benzo, substituted aryl, hydroxy, halogen, amino, alkylamino, nitro, cyano, $CF_3$, $OCF_3$, COPh, $COOCH_3$, $CONH_2$, CONHR, NHCONHR1, and NHCOR1; and wherein R1 is selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings containing one or more heteroatoms, and substituted heterocyclic rings; and wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl, and substituted heterocyclic rings are selected from the group consisting of alkyl, aryl, $CF_3$, $CH_3$, $OCH_3$, OH, COOR, COOH, and heterocyclic rings.

2. The pharmaceutical composition of claim 1, further comprising at least one additional ingredient.

3. The pharmaceutical composition of claim 2, wherein said at least one additional ingredient is selected from the group consisting of a short-acting β2-adrenergic agonist, a long acting β2-adrenergic agonist, an antihistamine, a phosphodiesterase inhibitor, an anticholinergic agent, a corticosteroid, an inflammatory mediator release inhibitor and a leukotriene receptor antagonist.

4. A method for treating an allergic reaction in a mammal in need thereof wherein said reaction is caused by an increase in IgE levels comprising administering an IgE-suppressing amount of a composition comprising at least one compound of claim 1.

5. The method of claim 4 further comprising administering at least one additional ingredient.

6. The method of claim 5, wherein said additional ingredient is selected from the group consisting of a short-acting $β_2$-adrenergic agonist, a long-acting $β_2$-adrenergic agonist, an antihistamine, a phosphodiesterase inhibitor, an anticholinergic agent, a corticosteroid, an inflammatory mediator release inhibitor and a leukotriene receptor antagonist.

7. A method for treating asthma in a mammal in need thereof comprising administering an IgE-suppressing amount of a composition comprising at least one compound of claim 1.

8. The method of claim 7 further comprising administering at least one additional ingredient.

9. The method of claim 8, wherein said additional ingredient is selected from the group consisting of a short-acting $β_2$-adrenergic agonist, a long-acting $β_2$-adrenergic agonist, an antihistamine, a phosphodiesterase inhibitor, an anticholinergic agent, a corticosteroid, an inflammatory mediator release inhibitor and a leukotriene receptor antagonist.

10. The pharmaceutical composition of claim 1, wherein the compound is from Genus A.

11. The pharmaceutical composition of claim 10, wherein the compound is selected from the group consisting of:

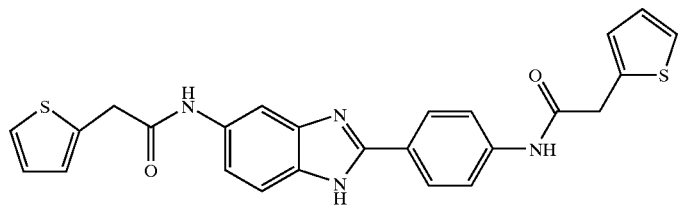

S-4

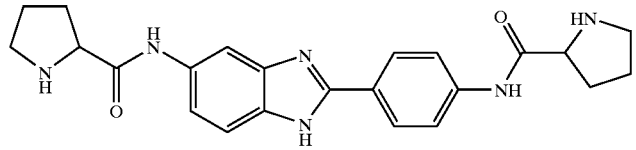

S-6

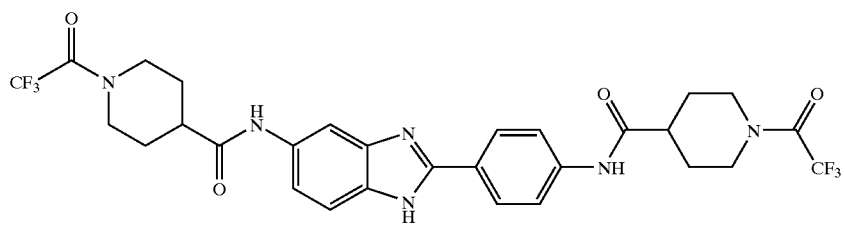

S-7

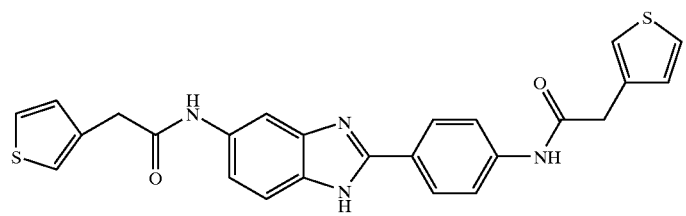
S-13
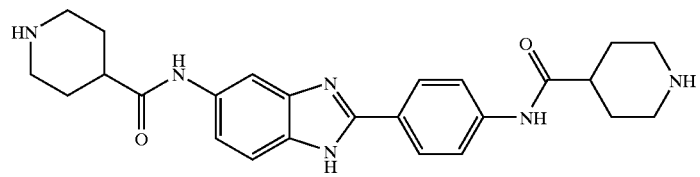
S-14
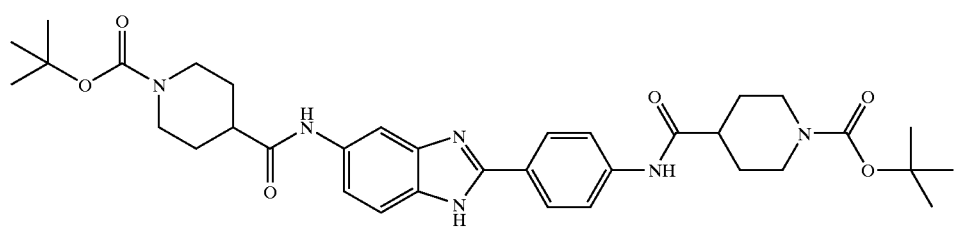
S-59
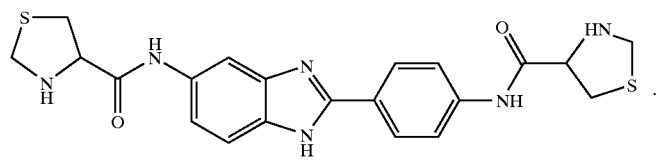
S-91
12. The pharmaceutical composition of claim 1, wherein the compound is from Genus B.
13. The pharmaceutical composition of claim 12, wherein the compound is selected from the group consisting of:
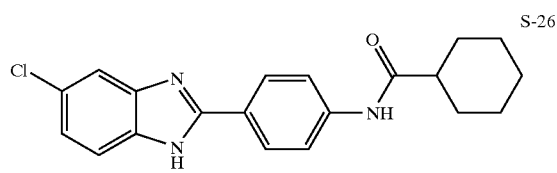
S-26
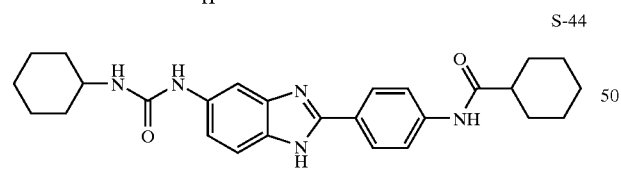
S-44
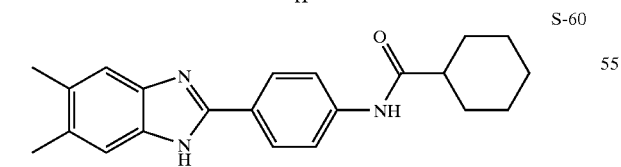
S-60
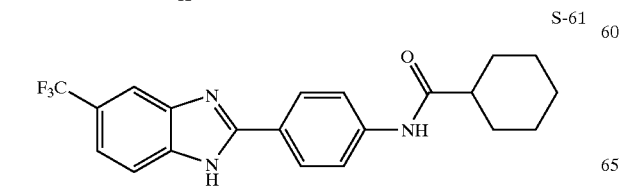
S-61
-continued
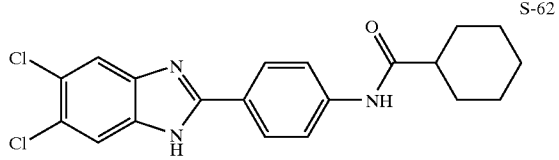
S-62
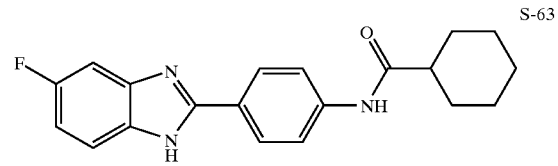
S-63
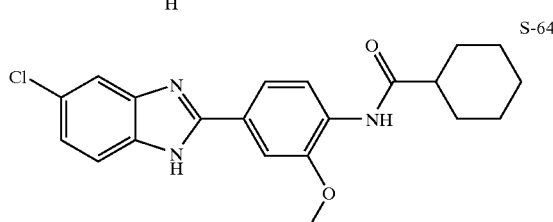
S-64
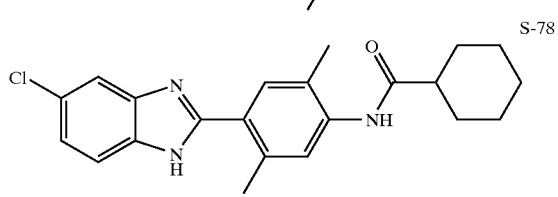
S-78

14. A pharmaceutical composition for treating an allergic reaction associated with increased IgE levels in a mammal in need thereof comprising one or more of the following compounds:

Genus (A)

wherein X and Y are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2C_6H_4$—F (p-); and wherein R1 and R2 are independently selected from the group consisting of alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, and substituted adamantyl, wherein R1 and R2 cannot both be methyl groups.

15. A method for treating an allergic reaction in a mammal in need thereof comprising administering an IgE-suppressing amount of at least one compound of claim 14.

16. A method of preparing a compound or salt thereof having the formula:

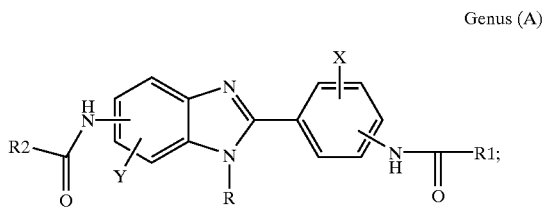

Genus (A)

wherein X and Y are independently selected from the group consisting H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2C_6H_4$—F (p-);

wherein R1 and R2 are independently selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings, and substituted heterocyclic rings;

wherein R1 and R2 cannot both be methyl groups;

wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl and substituted heterocyclic rings are selected from the group consisting of alkyl, acyl, aryl, $CF_3$, $CH_3$, $OCH_3$, OH, CN, COOR, COOH, $COCF_3$, and heterocyclic rings; and wherein at least one of R1, R2 or said substituents is a heterocyclic ring;

wherein said method comprises:

reacting a diaminonitrobenzene with an aminobenzoic acid to yield a first intermediate or salt thereof;

acylating said first intermediate or salt thereof to yield a second intermediate or salt thereof;

reducing said second intermediate or salt thereof to yield a third intermediate or salt thereof; and acylating said third intermediate or salt thereof to yield said compound or salt thereof.

17. A method of preparing a compound or salt thereof having the formula:

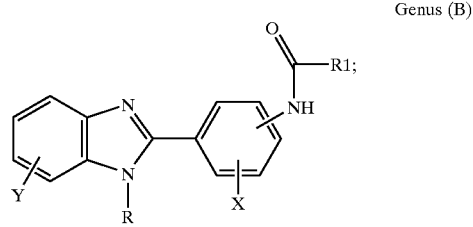

Genus (B)

wherein X is selected from the group consisting of mono, di, tri, and tetra substituted H, alkyl, alkoxy, aryl, substituted aryl, hydroxy, halogen, amino, alkylamino, nitro, cyano, $CF_3$, $OCF_3$, $CONH_2$, CONHR, and NHCOR1;

wherein R is selected from the group consisting of H, $CH_3$, $C_2H_5$, $C_3H_7$, $C_4H_9$, $CH_2Ph$, and $CH_2C_6H_4$—F (p-);

wherein Y is selected from the group consisting of mono, di, tri, and tetra substituted H, alkyl, alkoxy, aryl, benzo, substituted aryl, hydroxy, halogen, amino, alkylamino, nitro, cyano, $CF_3$, $OCF_3$, COPh, $COOCH_3$, $CONH_2$, CONHR, NHCONHR1, and NHCOR1; and wherein R1 is selected from the group consisting of alkyl, substituted alkyl, cycloalkyl, substituted cycloalkyl, multi-ring cycloalkyl, fused-ring aliphatic, cyclopropyl, substituted cyclopropyl, cyclobutyl, substituted cyclobutyl, cyclopentyl, substituted cyclopentyl, cyclohexyl, substituted cyclohexyl, cycloheptyl, substituted cycloheptyl, bicycloheptyl, bicyclooctyl, bicyclononyl, substituted bicycloalkenyl, adamantyl, substituted adamantyl, heterocyclic rings containing one or more heteroatoms, and substituted heterocyclic rings; and wherein the substituents on said substituted alkyl, substituted cycloalkyl, substituted cyclopropyl, substituted cyclobutyl, substituted cyclopentyl, substituted cyclohexyl, substituted cycloheptyl, substituted bicycloalkenyl, substituted adamantyl, and substituted heterocyclic rings are selected from the group consisting of alkyl, aryl, $CF_3$, $CH_3$, $OCH_3$, OH, CN, COOR, COOH, and heterocyclic rings;

wherein said method comprises:

reacting a diaminobenzene with an aminobenzoic acid to yield a first intermediate or salt thereof; and acylating said first intermediate or salt thereof to yield said compound or salt thereof.

18. The pharmaceutical composition of claim 10, wherein the compound is

S-13

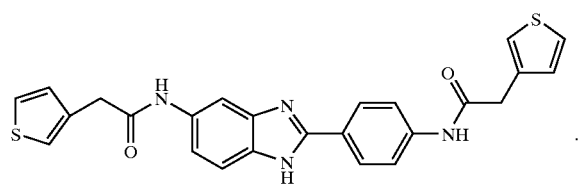

* * * * *

UNITED STATES PATENT AND TRADEMARK OFFICE
CERTIFICATE OF CORRECTION

PATENT NO. : 6,911,462 B2
DATED : June 28, 2005
INVENTOR(S) : Jagadish C. Sircar et al.

It is certified that error appears in the above-identified patent and that said Letters Patent is hereby corrected as shown below:

<u>Title page,</u>
Item [60], Related U.S. Application Data, "May 21, 1998" should be changed to -- May 22, 1998. --.

Signed and Sealed this

Thirtieth Day of August, 2005

JON W. DUDAS
*Director of the United States Patent and Trademark Office*